(12) United States Patent
Chmielewski et al.

(10) Patent No.: US 11,353,535 B2
(45) Date of Patent: Jun. 7, 2022

(54) REDUCTION OF ARTIFACTS IN MAGNETIC RESONANCE IMAGING

(71) Applicant: ViewRay Technologies, Inc., Oakwood Village, OH (US)

(72) Inventors: Thomas Chmielewski, Aurora, OH (US); Shmaryu M. Shvartsman, Highland Heights, OH (US)

(73) Assignee: VIEWRAY TECHNOLOGIES, INC., Oakwood Village, OH (US)

(*) Notice: Subject to any disclaimer, the term of this patent is extended or adjusted under 35 U.S.C. 154(b) by 187 days.

(21) Appl. No.: 15/933,288

(22) Filed: Mar. 22, 2018

(65) Prior Publication Data

US 2018/0275238 A1 Sep. 27, 2018

Related U.S. Application Data

(60) Provisional application No. 62/474,963, filed on Mar. 22, 2017.

(51) Int. Cl.
*G01R 33/565* (2006.01)
*G01R 33/381* (2006.01)
*G01R 33/383* (2006.01)

(52) U.S. Cl.
CPC ..... *G01R 33/56563* (2013.01); *G01R 33/381* (2013.01); *G01R 33/383* (2013.01); *G01R 33/565* (2013.01)

(58) Field of Classification Search
CPC ............ G01R 33/565; G01R 33/5659; G01R 33/287; G01R 33/387; G01R 33/381; G01R 33/383

USPC .................................................. 324/300–322
See application file for complete search history.

(56) References Cited

U.S. PATENT DOCUMENTS

| | | | | |
|---|---|---|---|---|
| 5,313,163 A | * | 5/1994 | Hardy | G01R 33/446 324/309 |
| 5,386,190 A | * | 1/1995 | Takeuchi | G01R 33/56563 324/309 |
| 5,438,264 A | * | 8/1995 | Takeshima | H01F 7/0278 324/319 |

(Continued)

FOREIGN PATENT DOCUMENTS

| JP | 2003135419 | 5/2003 |
|---|---|---|
| WO | 2012021848 | 2/2012 |

(Continued)

OTHER PUBLICATIONS

Poser et al., BOLD Contrast Sensitivity Enhancement and Artifact Reduction With Multiecho EPI: Parallel-Acquired Inhomogeneity-Desensitized fMRI. Magnetic Resonance in Medicine 55:1227-1235. (2006) (Year: 2006).*

(Continued)

*Primary Examiner* — Dixomara Vargas
*Assistant Examiner* — Sean Curtis
(74) *Attorney, Agent, or Firm* — Pillsbury Winthrop Shaw Pittman LLP

(57) ABSTRACT

Apparatuses, methods, and computer program products for reducing an appearance of an artifact in an image generated by a magnetic resonance imaging (MRI) system are disclosed. The apparatus includes a magnetic field generating device configured to create an inhomogeneity in the magnetic field of an MRI system and prevent at least one out-of-field excitation during imaging.

25 Claims, 20 Drawing Sheets

(56) References Cited

U.S. PATENT DOCUMENTS

| | | | | |
|---|---|---|---|---|
| 5,600,245 | A * | 2/1997 | Yamamoto | G01R 33/385 324/318 |
| 6,157,853 | A * | 12/2000 | Blume | A61B 34/70 606/130 |
| 6,212,419 | B1 * | 4/2001 | Blume | A61B 34/73 600/407 |
| 6,218,838 | B1 * | 4/2001 | McGinley | G01R 33/383 324/320 |
| 6,304,768 | B1 * | 10/2001 | Blume | A61B 34/70 600/407 |
| 6,323,646 | B1 * | 11/2001 | Zhou | G01R 33/56341 324/309 |
| 6,404,197 | B1 * | 6/2002 | Anderson | G01R 33/383 324/307 |
| 6,411,187 | B1 * | 6/2002 | Rotem | G01R 33/3806 335/298 |
| 6,456,077 | B2 * | 9/2002 | van Oort | G01R 33/3873 324/319 |
| 6,507,751 | B2 * | 1/2003 | Blume | A61B 34/70 600/407 |
| 6,647,134 | B1 | 11/2003 | McGee | |
| 6,680,663 | B1 * | 1/2004 | Lee | G01R 33/383 335/302 |
| 6,795,723 | B1 * | 9/2004 | Liu | G01R 33/4835 324/307 |
| 7,091,720 | B2 * | 8/2006 | Heubes | G01R 33/56563 324/309 |
| 7,190,247 | B2 * | 3/2007 | Zimmerling | H02K 35/02 335/207 |
| 7,250,762 | B2 * | 7/2007 | King | G01R 33/56518 324/309 |
| 7,262,678 | B2 * | 8/2007 | Tan | G01R 33/3806 335/302 |
| 7,498,809 | B2 * | 3/2009 | Takahashi | G01R 33/4833 324/309 |
| 7,511,490 | B2 * | 3/2009 | Abe | G01R 33/5613 324/309 |
| 7,952,351 | B2 * | 5/2011 | King | G01R 33/56518 324/309 |
| 7,977,946 | B2 * | 7/2011 | Teklemariam | G01R 33/3806 324/319 |
| 8,035,388 | B2 * | 10/2011 | Casanova | G01R 33/383 324/320 |
| 8,536,870 | B2 * | 9/2013 | Punchard | G01R 33/3875 324/322 |
| 8,593,144 | B2 * | 11/2013 | Marble | G01R 33/5617 324/309 |
| 8,639,006 | B2 | 1/2014 | Dempsey | |
| 8,847,594 | B2 * | 9/2014 | Zhou | G01R 33/56518 324/309 |
| 8,896,310 | B2 * | 11/2014 | Rapoport | G01R 33/383 324/319 |
| 8,929,638 | B2 | 1/2015 | Dempsey | |
| 8,952,691 | B2 * | 2/2015 | Blumich | G01R 33/44 324/303 |
| 9,222,998 | B2 * | 12/2015 | Teklemariam | G01R 33/383 |
| 9,429,673 | B2 * | 8/2016 | Walsh | G01V 3/14 |
| 9,448,294 | B2 * | 9/2016 | Rapoport | G01R 33/383 |
| 9,488,709 | B2 * | 11/2016 | Den Harder | G01R 33/56536 |
| 9,575,152 | B1 * | 2/2017 | Damadian | G01R 33/5659 |
| 9,678,184 | B2 * | 6/2017 | Nakanishi | G01R 33/56563 |
| 9,753,113 | B2 * | 9/2017 | Blumhagen | G01R 33/56572 |
| 9,869,741 | B2 * | 1/2018 | Blumhagen | G01R 33/56563 |
| 9,999,380 | B1 * | 6/2018 | Demas | A61B 5/05 |
| 10,048,335 | B2 * | 8/2018 | Matsunaga | G01R 33/445 |
| 10,094,896 | B2 * | 10/2018 | Rapoport | G01R 33/383 |
| 10,228,336 | B2 * | 3/2019 | Seltzer | G01R 33/3808 |
| 10,281,538 | B2 * | 5/2019 | Mathieu | G01R 33/3804 |
| 10,473,943 | B1 * | 11/2019 | Hughes | G02B 27/0905 |
| 10,661,098 | B2 * | 5/2020 | Leach | A61N 5/1039 |
| 11,275,143 | B2 * | 3/2022 | Köhler | G01R 33/56518 |
| 2001/0021805 | A1 * | 9/2001 | Blume | A61B 34/73 600/407 |
| 2001/0033167 | A1 * | 10/2001 | van Oort | G01R 33/3873 324/318 |
| 2002/0016542 | A1 * | 2/2002 | Blume | A61B 34/70 600/407 |
| 2003/0006770 | A1 * | 1/2003 | Smith | F23C 9/00 324/309 |
| 2004/0066194 | A1 * | 4/2004 | Slade | G01V 3/32 324/318 |
| 2004/0155659 | A1 * | 8/2004 | Prado | G01R 33/3806 324/309 |
| 2005/0017719 | A1 * | 1/2005 | Heubes | G01R 33/56563 324/309 |
| 2006/0091884 | A1 * | 5/2006 | Takahashi | G01R 33/4833 324/309 |
| 2006/0202788 | A1 * | 9/2006 | Tan | G01R 33/383 335/296 |
| 2007/0007960 | A1 * | 1/2007 | King | G01R 33/5617 324/309 |
| 2007/0262776 | A1 * | 11/2007 | Petropoulos | G01R 33/3873 324/318 |
| 2008/0137080 | A1 | 6/2008 | Bodzin | |
| 2009/0039882 | A1 * | 2/2009 | King | G01R 33/56518 324/307 |
| 2009/0072939 | A1 * | 3/2009 | Shen | G01R 33/383 335/306 |
| 2009/0206837 | A1 * | 8/2009 | Teklemariam | G01R 33/383 324/309 |
| 2009/0237080 | A1 * | 9/2009 | Kato | G01R 33/3873 324/319 |
| 2010/0013474 | A1 * | 1/2010 | Casanova | G01R 33/383 324/307 |
| 2010/0148777 | A1 * | 6/2010 | Marble | G01R 33/5617 324/318 |
| 2010/0171498 | A1 | 7/2010 | Auslender | |
| 2011/0241667 | A1 * | 10/2011 | Blumich | G01R 33/561 324/303 |
| 2011/0288407 | A1 | 11/2011 | Brinks | |
| 2012/0025826 | A1 * | 2/2012 | Zhou | G01R 33/56518 324/309 |
| 2012/0119742 | A1 * | 5/2012 | Rapoport | G01R 33/3802 324/318 |
| 2012/0124806 | A1 * | 5/2012 | Rapoport | G01R 33/3802 29/428 |
| 2014/0002080 | A1 * | 1/2014 | Den Harder | G01R 33/445 324/309 |
| 2014/0070803 | A1 * | 3/2014 | Jin | G01R 33/5605 324/309 |
| 2014/0084927 | A1 * | 3/2014 | Walsh | G01V 3/14 324/322 |
| 2014/0125333 | A1 * | 5/2014 | Hanada | G01R 33/56572 324/318 |
| 2014/0155732 | A1 * | 6/2014 | Patz | A61B 5/08 600/410 |
| 2014/0327440 | A1 * | 11/2014 | Nakanishi | G01R 33/3875 324/309 |
| 2015/0059157 | A1 * | 3/2015 | Rapoport | G01R 33/3802 29/525.08 |
| 2015/0200046 | A1 * | 7/2015 | Park | A61B 5/0042 335/302 |
| 2015/0260815 | A1 * | 9/2015 | Nishihara | G01R 33/4836 324/309 |
| 2016/0144200 | A1 * | 5/2016 | Leach | A61N 5/1077 324/322 |
| 2017/0059497 | A1 * | 3/2017 | Seltzer | G01R 33/3808 |
| 2017/0227621 | A1 * | 8/2017 | Hirai | G01R 33/56572 |
| 2018/0275238 | A1 * | 9/2018 | Chmielewski | G01R 33/383 |
| 2019/0076080 | A1 * | 3/2019 | Prado | A61B 5/4244 |
| 2019/0212298 | A1 * | 7/2019 | Goodwill | G01R 33/00 |

(56) References Cited

U.S. PATENT DOCUMENTS

2019/0250226 A1* 8/2019 Rapoport ............. G01R 33/383
2020/0072926 A1* 3/2020 Vogel ................... G01R 33/383

FOREIGN PATENT DOCUMENTS

| WO | WO-2016021603 A1 * | 2/2016 | ............. A61B 5/055 |
| WO | WO-2017134635 A1 * | 8/2017 | ............. G01N 24/08 |
| WO | WO-2018175807 A1 * | 9/2018 | ........... G01R 33/381 |

OTHER PUBLICATIONS

Tincher et al., Polynomial Modeling and Reduction of RF Body Coil Spatial Inhomogeneity in MRI. IEEE Transactions on Medical Imaging, vol. 12, No. 2, Jun. 1993 (Year: 1993).*

* cited by examiner

REDUCTION OF ARTIFACTS IN MAGNETIC RESONANCE IMAGING

CROSS-REFERENCE TO RELATED APPLICATIONS

The current application claims priority under 35 U.S.C. § 119 to U.S. Provisional Patent Application No. 62/474,963 filed Mar. 22, 2017 and entitled "Reduction of Artifacts In Magnetic Resonance Imaging," the contents of which are hereby incorporated by reference in their entirety.

BACKGROUND

Magnetic resonance imaging ("MRI") is a medical imaging technique that can be used in generating images of the interior of a patient, including healthy and diseased tissues. MRI scanners typically use strong magnetic fields, radio waves, and field gradients to generate such images. MRI systems are widely used by various medical facilities, such as hospitals, clinics, research facilities, etc.

Generally, in an MRI system, a substantially uniform main magnetic field, Bo, is created to cover the entire region of an area or volume to be imaged. For example, a subject may be positioned within an MRI scanner which forms the strong magnetic field. In most medical applications, protons (hydrogen atoms) in tissues containing water molecules are used to create a signal that is processed to form the image. The static magnetic field tends to align the proton spins (e.g. their magnetic dipoles) in the direction of the field where they precess around the field's axis. Energy from an oscillating magnetic field is temporarily applied to the patient at an appropriate resonant frequency to excite the protons, thereby causing a flip of their spin states. The excited hydrogen atoms emit a radio frequency signal, which is measured by a receive coil. The contrast between different tissues may be determined by the rate at which excited atoms return to the equilibrium state.

SUMMARY

In some implementations, the current subject matter relates to an apparatus for reducing appearance of artifacts in magnetic resonance imaging (MRI). The apparatus can include a magnetic field generating device configured to create an inhomogeneity (e.g., a distortion) in magnetic field of an MRI system and prevent at least one out-of-field excitation (i.e., artifacts or other distortions that can appear on an MRI image produced by the MRI system) during imaging. The MRI system can include an imaging area and can generate a magnetic field characterized by a main magnetic field gradient.

In some implementations, the current subject matter can include one or more of the following optional features. The magnetic field generating device can include at least one permanent magnet. The magnetic field generating device can include at least one electromagnet.

In some implementations, the magnetic field generating device can include at least one array of magnets. The array of magnets can be arranged on a belt. In some implementations, the magnetic field generating device can be placed in a patient couch of the MRI system. Alternatively, the magnetic field generating device can be mounted in a bore of the MRI system. Further, the magnetic field generating device and a gradient coil of the MRI system can be configured to generate a larger field of view where out-of-field excitations (e.g., artifacts) can occur.

In some implementations, a net near magnetic field of the array of magnets can be greater than its net far magnetic field. The array of magnets can be positioned in the MRI system outside of the imaging area and corresponding to a location of an approximately null magnetic field gradient. Each magnet in the array of magnets can be positioned at a first distance away from an isocenter of the magnetic field generated by the MRI system. A first magnet in the array of magnets can generate a magnetic field having a direction along a direction of the magnetic field of the MRI system. A second magnet in the array of magnets can generate a magnetic field having a direction opposite the direction of the magnetic field of the MRI system. The array of magnets can reduce appearance of the artifact in the image produced by the MRI system.

In some implementations, the current subject matter relates to a method for reducing an appearance of an artifact in an image generated by the MRI. The method can include positioning an array of magnets in the MRI system outside of the imaging area and corresponding to a location of an approximately null magnetic field gradient. As stated above, the net near magnetic field of the array of magnets can be greater than its net far magnetic field. Each magnet in the array of magnets can be positioned at a first distance away from an isocenter of the magnetic field generated by the MRI system. The method can also include generating, using a first magnet in the array of magnets, a magnetic field having a direction along a direction of the magnetic field of the MRI system and, using a second magnet in the array of magnets, a magnetic field having a direction opposite the direction of the magnetic field of the MRI system. Further, the method can include reducing, using the array of magnets, an appearance of the artifact in the image produced by the MRI system.

In some implementations, the current subject matter can include one or more of the following optional features. At least one magnet in the array of magnets can be positioned in anti-parallel fashion to at least another magnet in the array of magnets. The magnetic field gradient can include X and/or Y magnetic field gradients. The array of magnets can be an array of alternating magnets. At least one magnet in the array of magnets can be oriented perpendicular to the magnetic field of the MRI system.

In some exemplary, non-limiting, implementations, the first magnet and the second magnet can be positioned a second distance apart. The second distance can be in a range of approximately 1 centimeter to approximately 7 centimeters. The first distance can be in a range of approximately 20 centimeters to approximately 40 centimeters. The first and second magnets in the array of magnets can be at least one of the following: identical magnets and different magnets. The net near magnetic field of the array of magnets can extend approximately 3 centimeters to approximately 15 centimeters away from the array of magnets.

In some implementations, the strength of the magnetic field generated by the first magnet can be substantially equal to the strength of the magnetic field generated by the second magnet. This can produce a cancellation of the magnetic fields generated by the first magnet and the second magnet when the first magnet and the at least one second magnet are positioned at the first distance.

In some implementations, the first magnet and the second magnet can include at least one of the following: a permanent magnet, an electromagnet, a temporary magnet, a metal, an alloy, and any combination thereof. The first magnet and the second magnet can be positioned proximate to gradient null outside the imaging area.

In some implementations, the artifact can include at least one of the following: an aliasing artifact, a spot, a band, a featherlike artifact, a cusp artifact, an annefact, a fold-over artifact, a feather artifact, a peripheral signal artifact, and any combination thereof.

In some implementations, the array of magnets can include a plurality of pairs of magnets, wherein magnets in each pair of magnets in the plurality of pairs of magnets are positioned apart from each other. The array of magnets can be attached to a surface coil of the MRI system. The magnetic field of the MRI system can be homogenous inside the imaging area of the MRI system based on the positioning of the array of magnets. In some implementations, the array of magnets can be coupled to a pad, the pad being coupled to a surface coil of the MRI system. In some exemplary implementations, the array of magnets can be configured to be coupled to a belt. The belt can be configured to be attached to a subject (e.g., a patient) at a third distance from the location of the approximately null magnetic field gradient.

In an interrelated aspect, an apparatus includes a housing and an array of magnets contained in the housing. The array of magnets have at least a first magnet and a second magnet arranged substantially anti-parallel to the first magnet.

In some implementations, the array of magnets can include magnet pairs having substantially anti-parallel magnets. In other variations, the array of magnets can include at least four magnet pairs having substantially anti-parallel magnets.

In other implementations, the housing can be configured to be at least partially flexible and to provide spacing between the first magnet and the second magnet. The housing can include receptacles configured to contain at least the first magnet and the second magnet. The receptacles can also be configured to facilitate removal, replacement, and reorientation of magnets contained therein.

In yet other implementations, the housing can include sections connected to cause the apparatus to be semi-flexible. The sections can be are rigid and connected by one or more hinges.

In some implementations, the array of magnets can include at least one permanent magnet or at least one electromagnet. The first magnet can be comprised of a metal that is substantially unmagnetized in the absence of an external magnetic field. The metal can be steel.

In other implementations, the first magnet can be oriented such that it will be magnetized substantially anti-parallel to the second magnet by an external main magnetic field of a magnetic resonance imaging system. The array of magnets can include pairs of magnets in a stacked configuration. The pairs of magnets can also include at least three pairs of magnets.

The details of one or more variations of the subject matter described herein are set forth in the accompanying drawings and the description below. Other features and advantages of the subject matter described herein will be apparent from the description and drawings, and from the claims.

BRIEF DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 13b illustrates an exemplary arrangement of pairs of magnets arranged in a stacked configuration, according to some implementations of the present disclosure;

When practical, similar reference numbers denote similar structures, features, or elements.

DETAILED DESCRIPTION

In some implementations, the current subject matter relates to an apparatus for reducing appearance of artifacts in magnetic resonance imaging (MRI). The apparatus can include a magnetic field generating device configured to create an inhomogeneity in the magnetic field of an MRI system and prevent at least one out-of-field excitation (e.g., artifacts) during imaging. The magnetic field generating device can include at least one permanent magnet, at least one electromagnet, and/or any other type of magnet(s)

and/or any combination thereof. Further, the magnetic field generating device can include an array of magnets, which can be arranged on a belt. Further, the magnetic field generating device can be placed in a patient couch of the MRI system. Alternatively, the magnetic field generating device can be mounted in a bore of the MRI system. Further, the gradient coil of the MRI system can be optimized to work with the magnetic field generating device to generate a larger field of view where out-of-field excitation can occur.

In some implementations, the current subject matter relates to a system and a method for reducing an appearance of an artifact in an image generated by a magnetic resonance imaging system. The MRI system can include an imaging area and can generate a magnetic field that can be characterized by a main magnetic field gradient. One or more magnets (e.g., an array and/or pairs of magnets and/or any number of magnets) can be positioned in the system in an anti-parallel fashion. The magnet array can have a far magnetic field and a near magnetic field, where the near magnetic field can be greater than the far magnetic field, e.g., by orders of magnitude. The magnets can be positioned in the MRI system outside of the imaging area and corresponding to a location of where X and Y field gradients are approximately null. Further, magnets can also be positioned at a distance away from an isocenter of the magnetic field of the MRI system. The magnets can be arranged to generate magnetic fields in opposite directions, which can produce a cancellation effect. The arrangement of magnets can cause reduction of appearance of artifacts in images produced by the MRI system. The artifacts are typically caused by signals generated in the area where X and Y gradients are approximately null.

Figure 1:
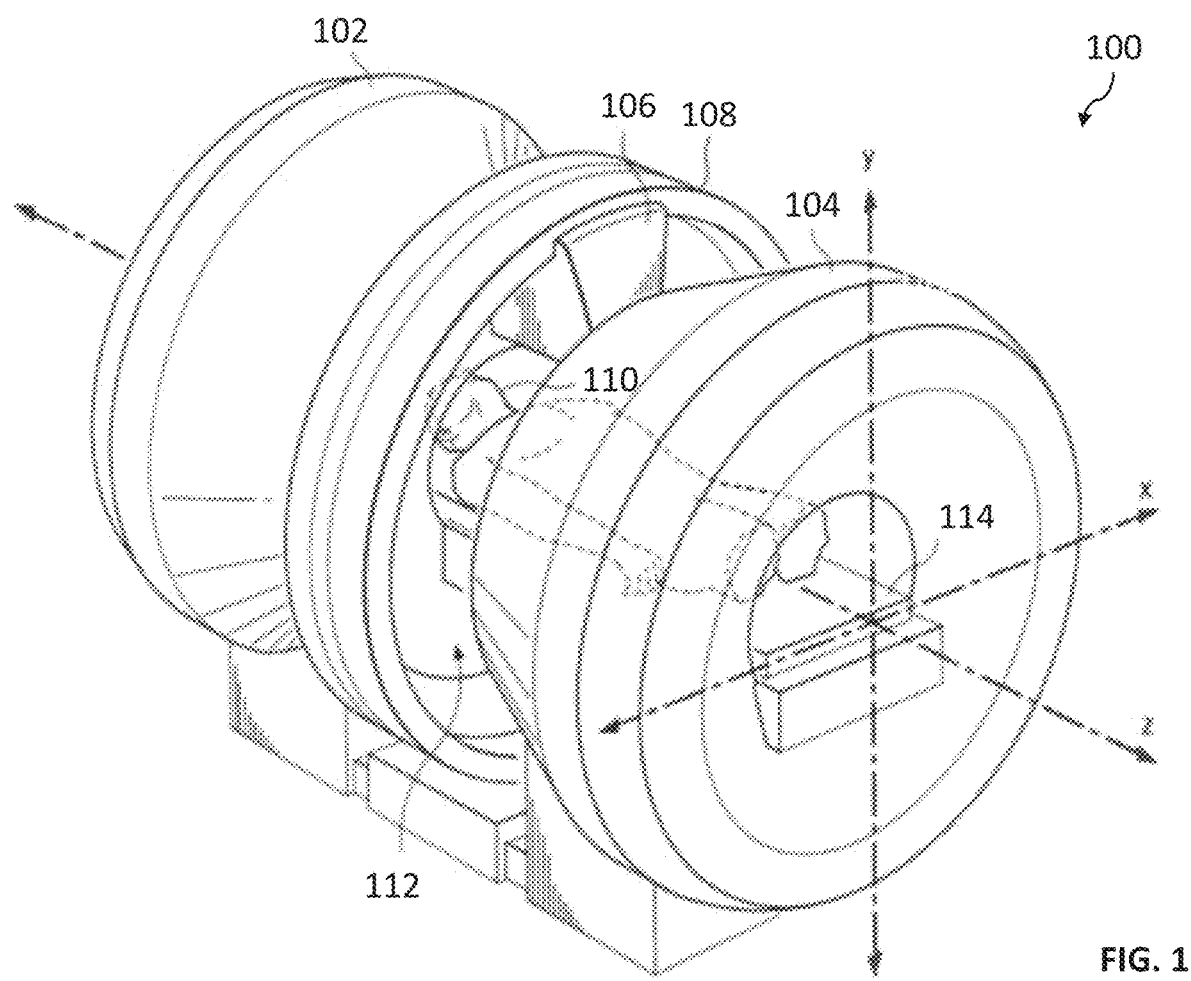
FIG. 1 illustrates an exemplary split MRI system.

FIG. 1 shows a perspective view of an exemplary split or "open" MRI system 100. The split MRI system 100 can include first and second magnet housings 102 and 104, which can be separated by a gap region 112. An instrument 106 can be mounted in the gap region 112 on a gantry 108. The instrument can include one or more radiation sources for delivering radiation to a target region. As shown in FIG. 1, a patient 110 can be positioned on a patient couch 114 inside of the first and second magnet housings 102, 104 and such that the gantry 108 can cause rotation of the instrument 106 to different positions relative to the patient 110 on the patient couch 114. For example, the gantry 108 can be used to reposition the instrument 106 about the patient 110 (e.g., at different angles of rotation about the Z-axis, as shown in FIG. 1).

While FIG. 1 illustrates a single assembly of the instrument 106, the current subject matter can include multiple assemblies mounted on the gantry 108, such as for example, multiple radiation emitters, multi-leaf collimator devices, etc., and/or any combination thereof. For example, some implementations can include three radiation head assemblies (not shown in FIG. 1) mounted in the gap 112, distributed about the Z-axis, and rotatable about the Z-axis on the gantry 108. The instrument 106 can include one or more radiation therapy devices, e.g., radiation sources and/or linear particle accelerators ("LINACs") and/or any type of instrument used with an MRI.

Figure 2:
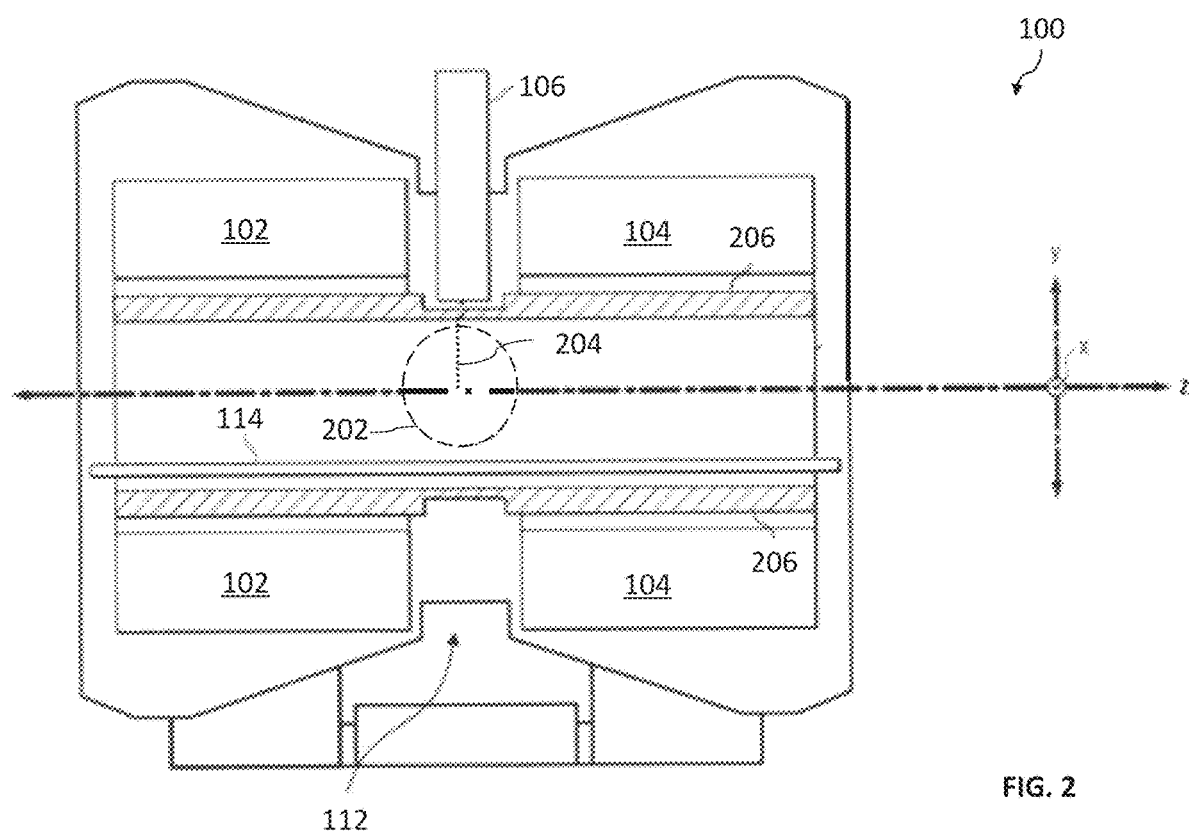
FIG. 2 illustrates a cross-sectional view of the exemplary split MRI system shown in FIG. 1.

FIG. 2 illustrates a cross-sectional view of the exemplary system 100 shown in FIG. 1. The system 100 can be used to image a target region 202 (e.g., a volume and/or area within the patient (not shown in FIG. 2), which can be positioned above the patient couch 114, while the instrument 106 can be used to emit radiation 204 for simultaneously performing a treatment to the patient within a target region 202. The system 100 can also include a radiofrequency transmit coil assembly 206 for transmitting radiofrequency ("RF") signals used for imaging. The system 100 can further include a RF receive coil assembly 210 that extends across the gap 104.

The system 100 can also include additional components, such as, gradient coils, one or more shim coils, etc. (not shown in FIGS. 1 and 2). The coordinate system used in the figures and throughout this disclosure refers to the longitudinal axis through the first and second magnet housings 102 and 104. The X-axis extends perpendicular to the Z-axis and from side-to-side of the first and second magnet housings 102 and 104. The Y-axis extends perpendicular to the X-axis and the Z-axis and from the bottom to the top of the first and second magnet housings 102 and 104.

As shown in FIG. 2, the RF coil assembly 206 can extend between the instrument 106 and the target region 202. For example, if the instrument 106 is a radiation emitting device (e.g., a device used with a radiotherapy system), a portion of the RF coil assembly 206 can be in the path of the radiation 204 that directed from the instrument 106 toward the target region 202.

Figure 3:
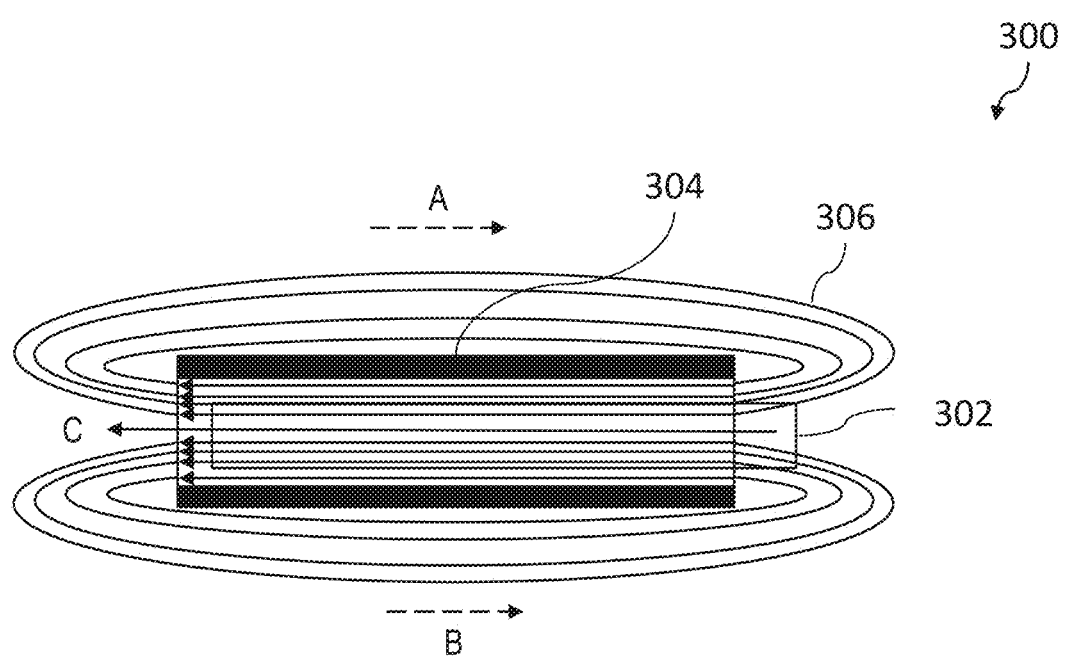
FIG. 3 illustrates general characteristics of a magnetic field.

Typically, MRI systems use strong magnetic fields, radio waves, and field gradients to generate images of the inside of the body. FIG. 3 illustrates general characteristics of a magnetic field, which are field direction and field strength. As shown in FIG. 3, a subject 302 can be positioned in the bore of the magnet 304. A magnetic field can be visualized by a series of parallel lines 306, where the arrows A, B, C indicate direction of the magnetic field. Electromagnets used for imaging produce a magnetic field that runs through the bore of the magnet and parallel to the major axis of the subject 302. As the magnetic field leaves the bore, it spreads out and encircles the magnet, thereby creating an external fringe field. Each point within a magnetic field has a particular intensity or strength, which is expressed tesla (T) or gauss (G) (1.0 T=10 kG). Magnetic field strengths of 0.15-3.0 T are typically used for imaging. Moreover, to produce quality images, MRI systems typically require their main magnetic field to be very uniform or homogeneous. Field homogeneity depends on magnet design, adjustments, and environmental conditions. MRI systems usually require a homogeneity on the order of a few parts per million (ppm) within the imaging area.

Figure 4:
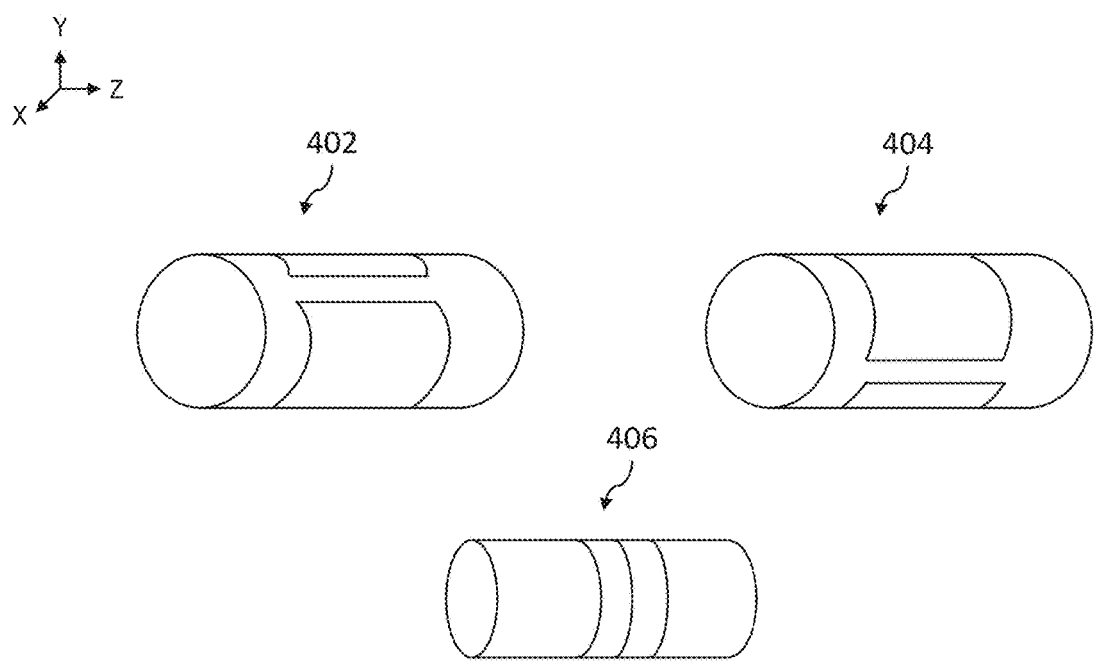
FIG. 4 illustrates exemplary gradient coils in an MRI system.

FIG. 4 illustrates gradient coils in an MRI system. When the MRI system is not producing an image, the magnetic field is uniform/homogeneous over the region of the subject. During the imaging process, the magnetic field is distorted with gradients. A gradient is a change in field strength from one point to another in the subject. When gradient coils are turned on (e.g., by applying an electric current), a gradient or variation in field strength is produced in the magnetic field. A typical MRI system can have three separate sets of gradient coils, which are oriented so that gradients are produced in the three orthogonal directions (x, y, z). Two or more of the gradient coils can be used together to generate a gradient in a particular direction. A gradient can be characterized by its strength, risetime, and slew-rate. A gradient's strength can be expressed in terms of a change in the magnetic field strength per distance (e.g., mT/m). A gradient's risetime is a time required for a gradient to reach its maximum strength and slew-rate is a rate at which the gradient changes with time.

As shown in FIG. 4, gradient coils 402 are generating gradient in an x-direction; gradient coils 404 are generating a gradient in a y-direction; and gradient coils 406 are generating a gradient in a z-direction. Typically, gradient coils are wrapped or pre-printed around a cylindrical surface. Gradient fields distort the main magnetic field in according to a pattern, which can allow spatial encoding of the magnetic resonance signal.

Images produced by the MRI system during the imaging process can contain various artifacts. An artifact can be a distortion in the produced image. Artifacts can be caused by various subject-related factors, e.g., voluntary and physiologic motion, metallic implants and/or foreign bodies. Artifacts and foreign bodies within the subject's body can be confused with pathology and/or can reduce the quality of an examination. There many different types of artifacts, e.g., a truncation artifact, a motion artifact, an aliasing artifact, etc. For example, artifacts can be caused by breathing, cardiac movement, foreign bodies found on and/or in subject's body, etc.

Figure 10A:
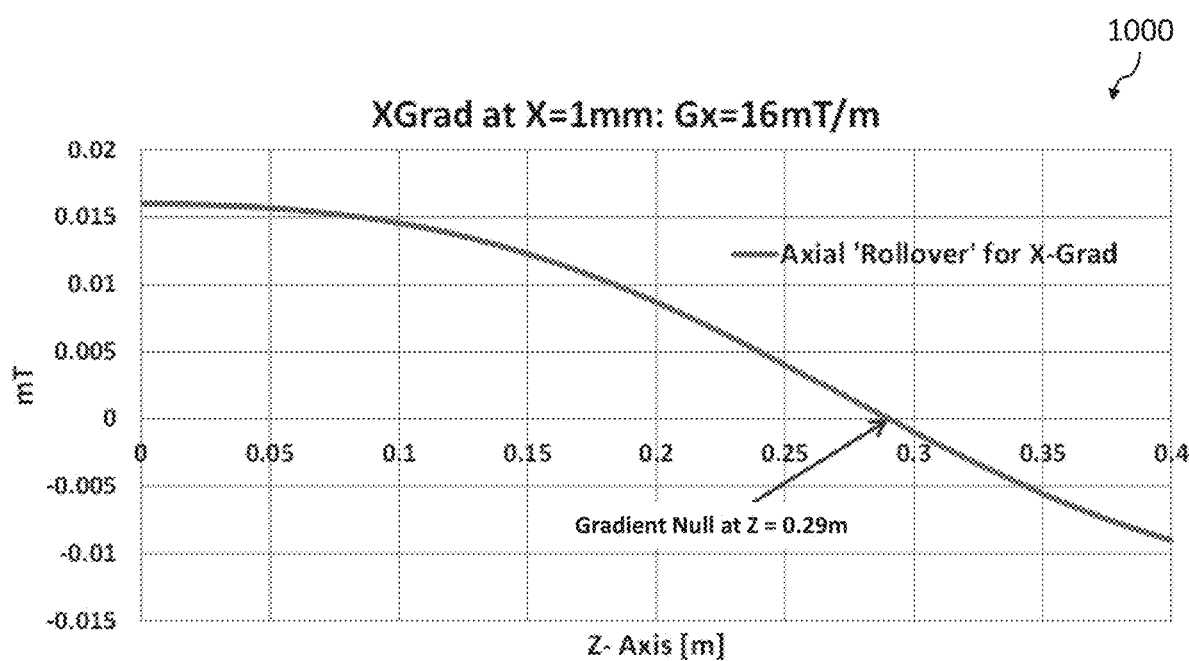
FIGS. 10a-b are plots that illustrate occurrence of a gradient null.
Figure 10B:
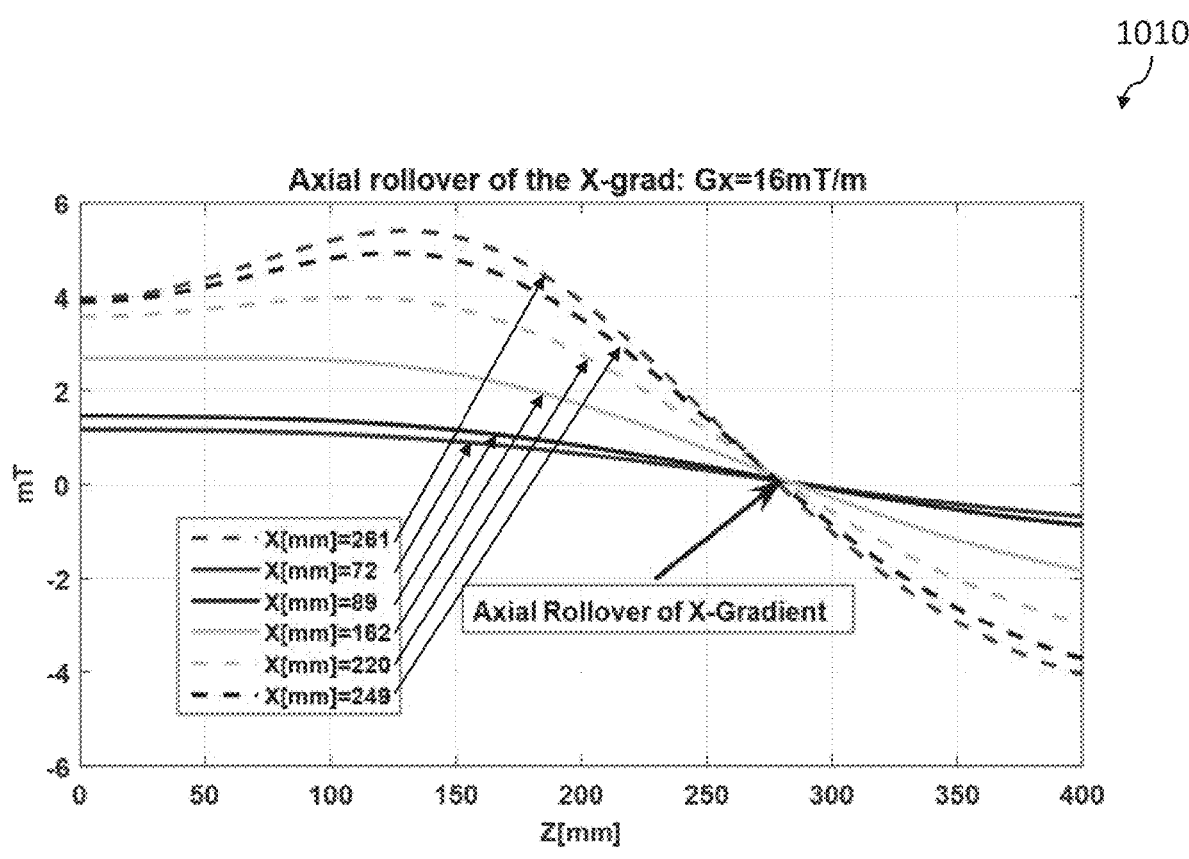

However, in MRI systems, an artifact can occur as a result of a "gradient null". A gradient null can cause un-encoded signal(s) to converge to high intensity outside the area of interest (e.g., area of interest on the subject). FIGS. 10a-b illustrate occurrences of a gradient null. FIG. 10a is a plot 1000 illustrating an X (and Y) gradient strength as a function of z position for single x position. FIG. 10b is a plot 1010 that illustrates an X (and Y) gradient strength as a function of z position for several x positions. As shown in FIG. 10a, the X gradient is initially linear at approximately 0.016 mT and z=0 position. However, as z changes (becomes greater than 0), a gradient "fall off" or "axial rollover" begins to occur. The X (and Y) gradient eventually crosses a 0 mark, where a gradient null occurs (i.e., here z=0.29 m). The main magnetic field continues to be uniform, thereby producing a substantial signal. This can cause formation of artifacts within the area of interest when certain scanning techniques are used. The artifacts produced in Cartesian imaging can include cusp artifacts, annefacts, foldover artifacts, feather artifacts, peripheral signal artifacts, etc. In non-Cartesian (e.g., real time spiral and radial) imaging, the artifacts can be much more apparent, which results in lines throughout the produced image, as for example shown in FIG. 11a. The current subject matter seeks to eliminate signals near the gradient null zones, and to thereby reduce appearance of artifacts.

The current subject matter can reduce and/or eliminate the above artifacts by manipulating a magnetic field near the undesired signal to minimize effects of the undesired signal. The magnetic field can be manipulated in many fashions to produce the desired result. In some implementations, the current subject matter can implement various methods to manipulate the magnetic field outside of the desired imaging area (near the gradient null), while minimally affecting the magnetic field within the imaging area.

Some implementations can include designing the gradient coil, or controlling operation of the gradient coil, to cause the gradient null area to be positioned axially towards or away from the isocenter (for example further out than illustrated in the figures of the present disclosure). In some implementations, moving the gradient null area to an axial location further from the isocenter (optionally in combination with any of the other embodiments described herein), can reduce the appearance of artifacts.

In some implementations, the gradient coil of the MRI system can be optimized for the purposes of generating a larger field of view where out-of-field excitations can occur. A field of view in the MRI system can be defined as a size of 2D or 3D spatial encoding area of an image produced by the MRI system. The field of view can be an area that can include an object of interest for imaging. The smaller the field of view, the higher the resolution and the smaller the voxel size and the lower the measured signal. In some cases, magnetic field homogeneity can decrease as more area/tissue is imaged (i.e., corresponding to a larger field of view). Magnetic field homogeneity can be measured in parts per million (ppm) over a particular diameter of spherical volume (DSV) and can correspond to a uniformity of a magnetic field in the center of the scanner when no object is present.

In some implementations, optimization of the gradient coil can be based on a uniformity parameter. The uniformity parameter can be defined as a ratio of gradient strengths at a particular point in the field of view. It can be represented by a slope of a curve (e.g., curves shown in FIGS. 10a-b) defining how "fast" the "axial rollover" of a z-component of the magnetic field (B) can occur along the z-axis. In particular, for any given $x_o$ point (for an X-gradient) in the field of view, the uniformity parameter can represent a ratio of the vector field's (B) z-component at a point $z_o$ to the z-component at a starting point of Z=0 (i.e., corresponding to $B_z(x_o, 0, 0)$):

$$\text{uniformity parameter} = \frac{B_z(x_o, 0, z_o)}{B_z(x_o, 0, 0)} \qquad (1)$$

The above equation (1) can be similarly rewritten for a Y-gradient:

$$\text{uniformity parameter} = \frac{B_z(0, y_o, z_o)}{B_z(0, y_o, 0)} \qquad (2)$$

Figure 10C:
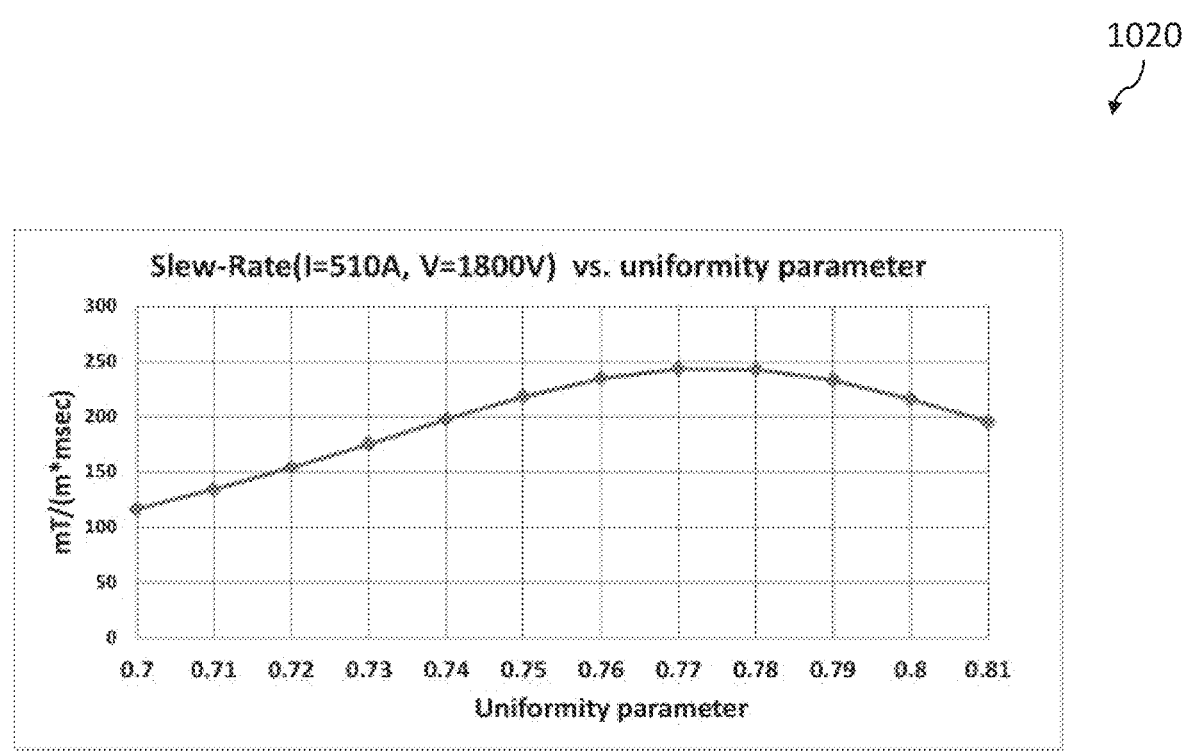
FIG. 10c illustrates an exemplary plot illustrating a relationship between a slew-rate parameter and a uniformity parameter.
Figure 10D:
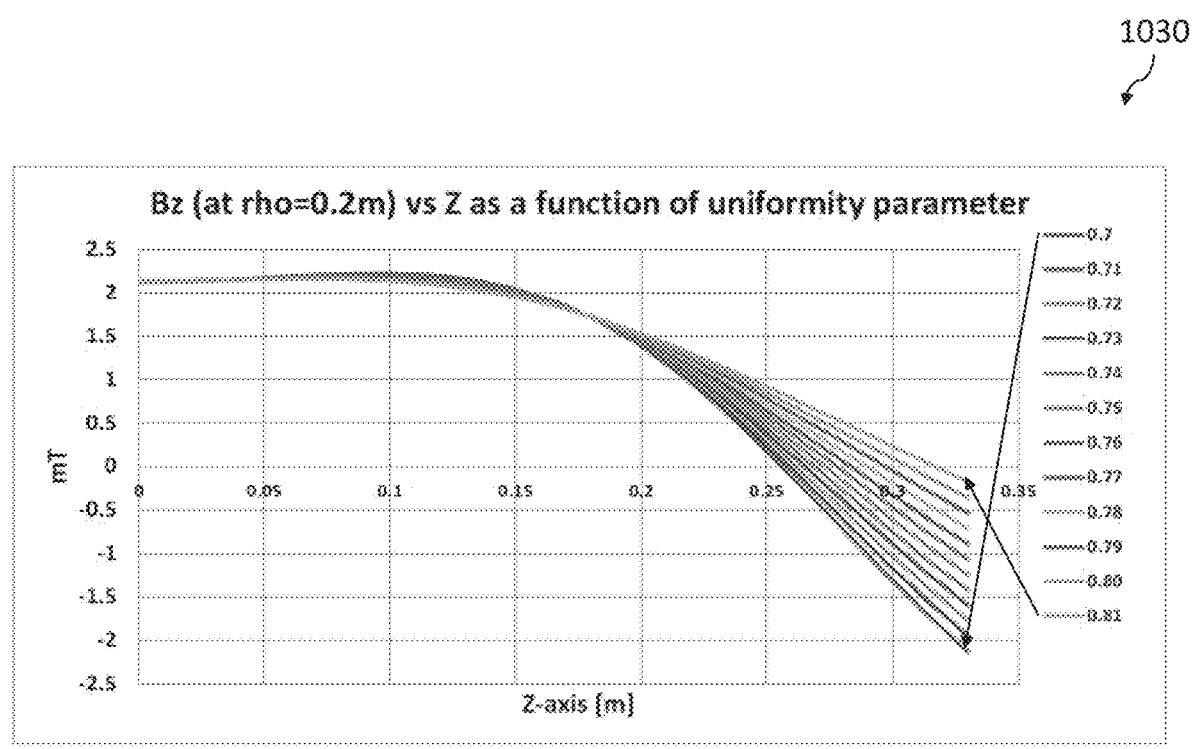
FIGS. 10d-e illustrate exemplary plots of a vector field's (B) z-component versus z-position as a function of the uniformity parameter.
Figure 10E:
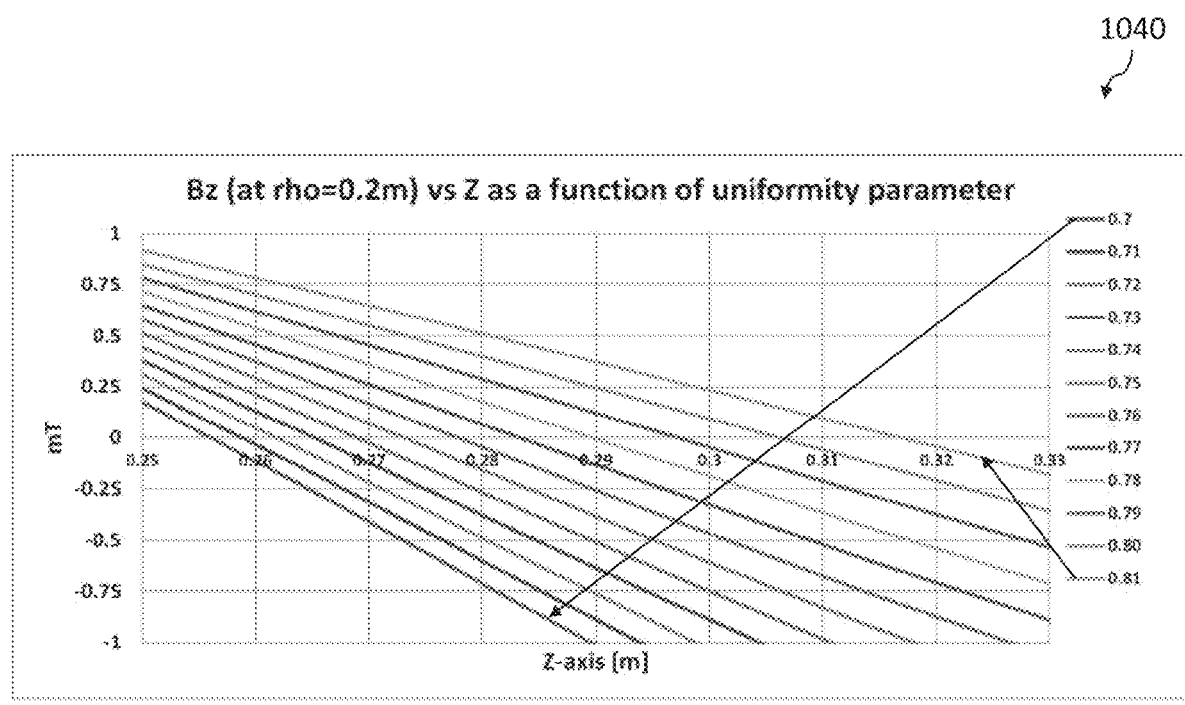

FIG. 10c illustrates an exemplary plot 1020 illustrating a relationship between a slew-rate parameter and the uniformity parameter. As shown in FIG. 10c, the slew-rate (mT/m) (i.e., rate at which the gradient changes with time) is measured at current I=510 A and voltage V=1800V. The slew-rate appears to peak when the uniformity parameter is approximately 0.77-0.78. FIG. 10d illustrates an exemplary plot 1030 (and FIG. 10e illustrates an enlargement 1040 of a portion of the plot 1030) of a vector field's (B) z-component versus z-position as a function of the uniformity parameter. As shown in FIGS. 10d-e (plots 1030-1040), axial rollover occurs for any value of the uniformity parameter. This means that the curve representative of the vector field's (B) z-component crosses the z-axis. If the axial rollover does not occur, the energy, inductance and rise time of the X (and Y) gradient can be infinitely large. Thus, the uniformity parameter can be used to ascertain and/or optimize performance of the gradient coil. For example, as shown in FIGS. 10c-e, for a transverse gradient (X or Y gradient), the uniformity parameter can be used to determine performance of a gradient coil for a particular gradient strength as well as determine spatial constraints (e.g., diameter, length, etc.) of the coil. It can also be used to determine total energy, inductance, slew-rate, and rise time. Further, the uniformity parameter can affect gradient coil spatial distortions (caused by gradient nonlinearity), i.e., greater uniformity parameter can reduce spatial gradient distortions.

Figure 5:
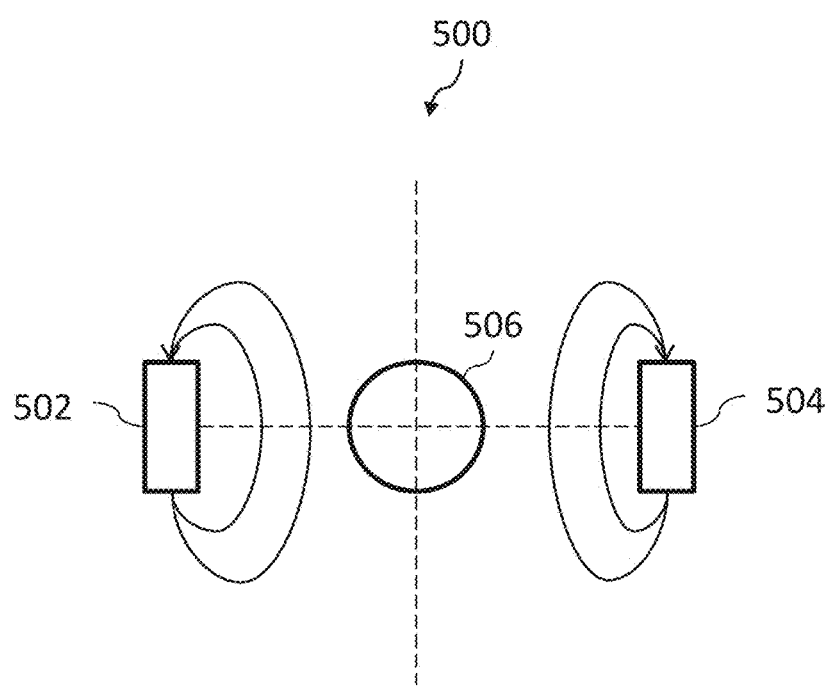
FIG. 5 illustrates an exemplary system for attenuating/removing artifacts in a magnetic resonance imaging system, according to some implementations of the current subject matter.

FIG. 5 illustrates an exemplary system 500 for attenuating/removing artifacts in a magnetic resonance imaging system, according to some implementations of the current subject matter. The system 500 can include a pair of magnets (and/or an array of magnets and/or any number of magnets) 502, 504. The magnets 502, 504 can be permanent magnets. The net near fields of the array or the permanent magnets can be configured to be strong and their net far fields configured to be weak. The magnets 502, 504 can be positioned apart. The magnets 502, 504 can be identical. In some implementations, each magnet in then pairs and/or an array of magnets 502, 504 (n is an integer greater than or equal to 1, greater than 4, etc.) can be spaced a distance apart from another magnet. In some exemplary implementations, the distance between the magnets can be experimentally determined (e.g., based on magnetic fields of the magnets, specifications of the system, images sought to be produced, etc.).

In some implementations, one of the magnets 502, 504 (e.g., magnet 502) can have its magnetic field aligned with the MRI systems' main magnetic field (not shown in FIG. 5) and the other one of the magnets 502, 504 (e.g., magnet 504) can have its magnetic field aligned opposite to the MRI system's main magnetic field. In the n-pairs and/or array of magnets implementation, one of the magnets in each pair can have its magnetic field aligned with the main magnetic field, while the other magnet in each pair can have its magnetic field be opposite the main magnetic field. In some implementations, the magnets can be alternately positioned so that there is a strong effect in the gradient null area while having little or no effect in the imaging area.

In some implementations, a separation between magnets 502, 504 can be so selected to optimize the performance (i.e., removal of artifacts). In some implementations, the magnets 502, 504 can be positioned around an area 506 where the gradient field converges. In a non-limiting, exemplary implementation, the magnets 502, 504 can be positioned 20-40 cm from an isocenter in the HF direction. Additionally, a distance between the magnets 502, 504 can also be selected to optimize performance (i.e., removal of artifacts).

In some exemplary, non-limiting implementations, the magnets can have a size of 1 inch by ½ inches by ⅛ inches. The magnets can be spaced 50 mm apart. Some magnets (e.g., at the end of an array of magnets (as discussed below) can be smaller (e.g., ½ of the above main magnets) and can be spaced 25 mm apart. As can be understood, any sizes and/or spacing of magnets can be implemented.

In the n-pairs of magnets implementation, each pair of magnets can also be spaced apart from another pair of magnets, as desired (e.g., based on magnetic fields of the magnets, specifications of the system, images sought to be produced, etc.). Further, the magnet pairs can be rigidly fixed relative to one another to ensure cancellation of the forces produced by a single magnet.

Figure 6:
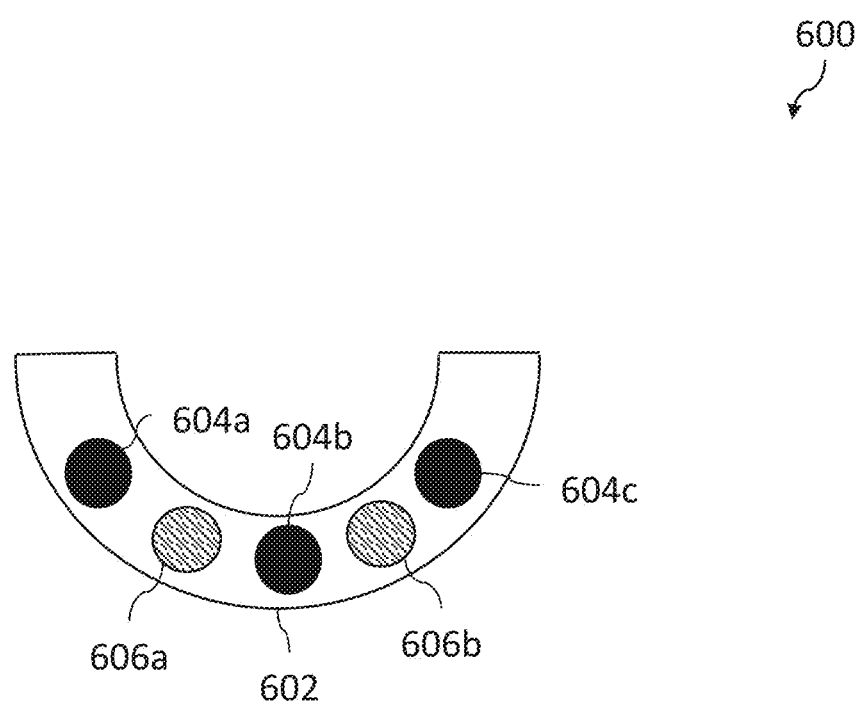
FIG. 6 illustrates an exemplary n-pairs of magnets system for attenuating/removing artifacts in a magnetic resonance imaging system, according to some implementations of the current subject matter.

FIG. 6 illustrates an exemplary magnet system 600 for attenuating/removing artifacts in a magnetic resonance imaging system, according to some implementations of the current subject matter. The system 600 can be configured to create an inhomogeneity in magnetic field of the MRI system and thereby prevent at least one out-of-field excitation during imaging. The magnets (and/or magnet polarity) of one or more magnet pairs can be arranged in an antiparallel (or substantially anti-parallel) way, where the orientation and/or polarity of one of the magnets is substantially opposite the orientation and/or polarity of another magnet. For example, magnet 604*a* and 604*b* are illustrated as being substantially anti-parallel to magnets 606*a* and 606*b*, respectively. As used herein, the term "substantially" means that the feature it modifies need not be exact. For example, the term "substantially anti-parallel" contemplates that the magnets are oriented to be nearly anti-parallel, but allows for some small deviations due to construction errors, design choices, and the like.

To provide particular implementations of field cancellation, the magnets (e.g., including a first magnet and a second magnet) can be oriented side-by-side (i.e., not end-to-end) to cause a north pole of the first magnet to be closer to a south pole of the second magnet than to a north pole of the second magnet.

When the present disclosure describes features of the orientation or disposition of the magnets, it is understood that such can be used with any of the implementations herein. For example, the terms above as they relate to the magnets described in FIG. 6 can apply to other embodiments of the magnets and apparatuses described throughout the disclosure.

In some implementations, one magnet's magnetic field can be aligned with the main magnetic field of the MRI system and the other magnet's magnetic field can be substantially opposite of the main magnetic field. In some exemplary implementations, the array can have n-pairs of magnets or any number of magnets.

As shown in FIG. 6, the system 600 can include an array housing 602 that contain magnets 604 (*a, b, c*) and 606(*a, b*). The magnets 604 and 606 can be arranged in a semi-circular array, as illustrated in FIG. 6. As can be understood, the magnets can be arranged in any desired housing, pattern, array, and/or any combination thereof. For example, a belt (e.g., flexible, rigid, semi-flexible, and/or semi-rigid) containing the magnets can be used for placement around the patient during an MRI procedure. The array housing 602 can be manufactured from any desired material, e.g., plastic, cloth, metal, etc. The magnets can be loose within the array housing 602 and/or can be permanently secured to the array housing 602 in any desired fashion (e.g., glued, welded, using snaps, hooks, etc.). In preferred implementations, the housing is constructed in a manner to substantially maintain a particular orientation and relative location of the magnets therein.

Magnets 604, 606 can be the same size and have same magnetic properties. Alternatively, the magnets 604, 606 can have varying sizes and/or varying magnetic properties. The array housing 602 can be configured to have magnets 604, 606 spaced apart. The distances separating each magnet can be the same and/or can vary from one pair of magnets to the next. As can be understood, the system 600 is not limited to the arrangement shown in FIG. 6. In particular, the magnets can be arranged in any desired fashion, using any type of housing, and the system 600 can include any number of magnets. Further, the magnets and/or pairs of magnets can be separated by any desired distances. The arrangement of magnets, the number of magnets, the distances separating the magnets, the strengths of the magnets' magnetic fields, the type of housing that can contain the magnets, etc., can be based on an effect that is desired to be achieved, images sought to be produced, particular artifacts to be removed or reduced, specifications of the MRI system, etc. In some implementation, the arrangement of magnets, the number of magnets, the distances separating the magnets, the strengths of the magnets' magnetic fields, the type of housing that can contain the magnets, etc. can be optimized in order to reduce and/or suppress occurrence of artifacts. The magnets (and/or magnet pairs and/or array(s) of magnets, etc.) can also be placed perpendicular to the main field. Further, positioning of each magnet can be dependent on the field that is to be disturbed, the imaging area, etc. Moreover, any number of magnets 604, 606 in the array 602 can be used to achieve a desired effect. In some implementations, perpendicular (and/or radial) positioning of the magnets with respect to the main magnet field can produce an improved performance as compared to when magnets are oriented parallel to the main field (as, for example, is shown in and discussed with respect to FIGS. 8a-9c).

As stated above, magnets 604, 606 can be arranged in an anti-parallel fashion in the array housing 602. The net near fields of the magnets 604, 604 can be strong, while their net far fields can be weak. For example, magnets 604 can be arranged to have their magnetic field to be along the main magnetic field of the MRI system (not shown in FIG. 6). By comparison, magnets 606 can be arranged to have their magnetic field to be opposite the main magnetic field of the MRI system. Such positioning and the nature of the magnetic fields of magnets 604, 606 can produce a cancellation effect, whereby the main imaging area is not affected by the presence of magnets 604, 606 in the array housing 602 and the presence of produced imaging artifacts is substantially reduced and/or eliminated.

In some implementations, the magnets can be positioned at a desired location on a surface coil of the MRI system (not shown in FIG. 6). This can ensure that the field being disturbed is the correct field relative to the location of the imaging area. In alternate implementations, the magnets can be positioned in a band or a belt that can be placed around the patient at the desired location (see, for example, FIG. 14). In some implementations, the magnets can be positioned in a patient couch of the MRI system. Alternatively, the magnets can be mounted in a bore of the MRI system. Further, the gradient coil of the MRI system can be optimized in relation to the magnets so a larger field of view, where out-of-field excitation can occur, can be generated.

In some exemplary implementations, one or more electromagnets can be used instead of the permanent magnets. Alternatively, a combination of magnets and other non-magnetized metals, such as steel or other ferromagnetic materials can be used. Accordingly, some implementations can include a second magnet (e.g., of any of the pairs of magnets) being a metal that can be magnetized substantially anti-parallel to the first magnet (in the pair of magnets) in response to an external magnetic field (e.g., the main MRI magnetic field). In such implementations, where the second magnet is a metal that is not initially a magnet, the second magnet can therefore be substantially unmagnetized in the absence of the external magnetic field. The present disclosure contemplates that the second magnet (which is not generally considered a magnetic material) may retain some magnetization. However, such incidental magnetization (i.e., being substantially unmagnetized) is understood to be small compared to the magnetization of the first magnet, which can be a permanent magnet, or small compared to the magnetic field generated during typical operation of an electromagnet (when the first magnet is such).

In other implementations, a permanent magnet can be included such that it is oriented to have a magnetization against (e.g., in the opposite direction of) the main magnetic field. Further, another element comprising a material that can be magnetized, such as steel, can placed such that it is magnetized along the main magnetic field, by the MRI's main magnetic field. The arrangement can continue by the addition of a second permanent magnet having the same magnetization as the first permanent magnet, and so on. The magnetization of the permanent magnets can be axial (e.g., substantially anti-parallel to the main magnetic field).

Figure 7:
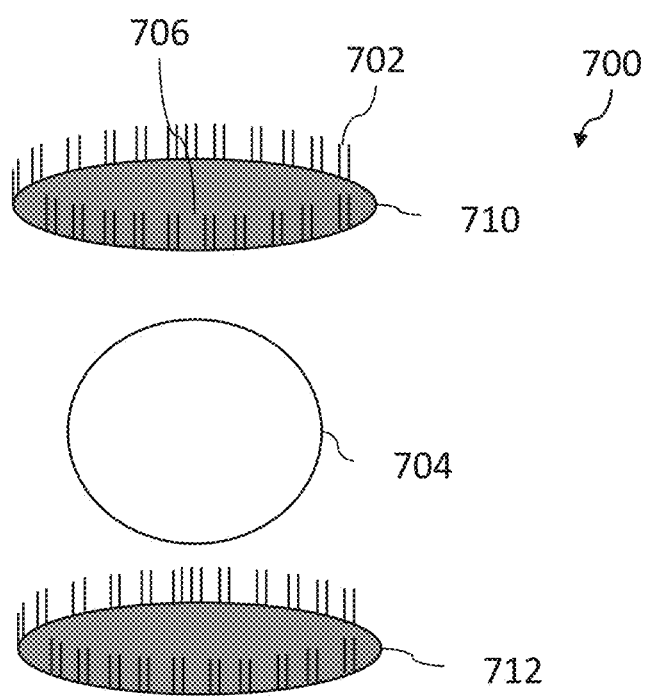
FIG. 7 illustrates an exemplary system for attenuating/removing artifacts in a magnetic resonance imaging system, according to some implementations of the current subject matter.

FIG. 7 illustrates an exemplary system 700 for attenuating/removing artifacts in a magnetic resonance imaging system, according to some implementations of the current subject matter. The system 700 can include an imaging area 704 and have a plurality of magnets 702 that can be arranged in a disc-like fashion, as shown by the discs 710, 712. The magnets can be arranged in any other fashion (e.g., using a belt that can be wrapped around the subject, etc.). The magnets can be positioned in an anti-parallel fashion (i.e., parallel to each other but in opposite directions). Further, the magnets 702 can be positioned at a location that can correspond to the where the main magnetic field gradient is approximately zero or null.

The pairs of magnets 702 can have a far magnetic field and a near magnetic field. The near magnetic field can be greater than the far magnetic field (e.g., by orders of magnitude).

The array of magnets 702 can be arranged at a distance from an isocenter in the direction of the main magnetic field. In some exemplary, non-limiting implementations, such distance can be approximately 30 cm. Further, the magnets can be positioned approximately 1-7 centimeters apart from each other. The pairs of magnets 702 can perturb the magnetic field in the area 706 of the disc 710 (similarly for the pairs of magnets arranged in the disc 712). The area 706 corresponds to a gradient null area. This is the area where gradients collapse, thereby generating an image artifact. At a distance away from the magnets (e.g., which can be approximately 350 mm) in the imaging area 704, the resulting field generated by the magnets can be approximately zero, thereby not affecting the imaging area 704.

In some implementations, the number, size, distance, and/or orientation of the array of magnets can be adjusted to optimize local effects and/or to minimize perturbation in the imaging area. In some exemplary, non-limiting implementations, the array of magnets can be arranged to have a substantially large local field (e.g., in a range >100 ppm) that can penetrate approximately 5-10 cm into the area 706, while having less than 5 ppm perturbation into the imaging area 704 (e.g., 35 cm). In some exemplary implementations, the net near magnetic field of the array of magnets can extend approximately 3 centimeters to approximately 15 centimeters away from the array of magnets.

Further, in some exemplary, non-limiting implementations, the array of magnets can be positioned approximately 20 centimeters to approximately 40 centimeters away from an isocenter of the main magnetic field and outside of the imaging area 704 and corresponding to a location where the X and/or Y field gradient(s) is approximately zero or null.

As stated above, the magnets in the array of magnets 702 can be at least one of the following: identical magnets and different magnets. Further, the strength of the magnetic field generated by each magnet can be substantially equal to the strength of the magnetic field generated by the other magnet. This can produce a cancellation of the magnetic fields generated by both magnets at particular locations.

In some implementations, the magnets in the array of magnets 702 can include at least one of the following: a permanent magnet, an electromagnet, a temporary magnet, a metal, an alloy, and any combination thereof. The artifacts that the pairs of magnets can attenuate can include at least one of the following: an aliasing artifact, a spot, a band, a featherlike artifact, a cusp artifact, an annefact, a fold-over artifact, a feather artifact, a peripheral signal artifact, any signal artifact resulting from un-encoded signal at the X and Y gradient nulls, and/or any combination thereof.

Further, the array of magnets 702 (as shown in FIG. 7) can be positioned at a given distance apart from each other. For example, pairs of magnets can be positioned in an array. Further, one or more pairs and/or alternating arrays of magnets can be attached to a surface coil of the MRI system. In some implementations, positioning of the pairs of magnets 702 can allow the main magnetic field to be homogenous inside the imaging area 704 of the MRI system.

Figure 8A:
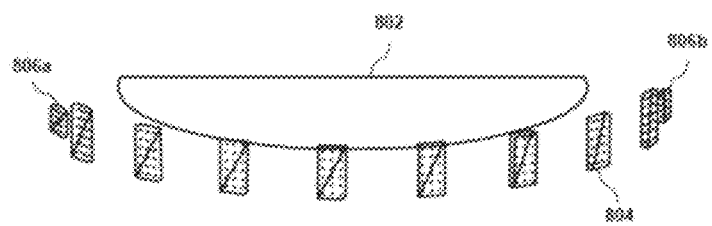
FIGS. 8a-c illustrate an exemplary array of magnets, according to some implementations of the current subject matter.
Figure 8B:
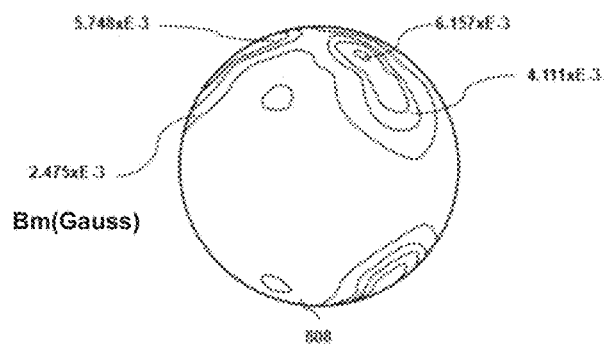
Figure 8C:
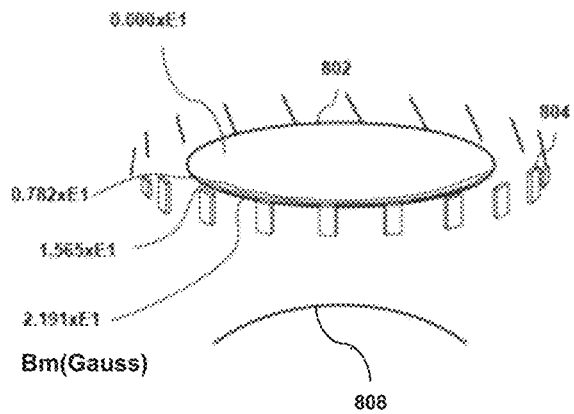

FIGS. 8a-c illustrate an exemplary array of magnets 804 and 806(a, b) that are oriented radially and arranged around a gradient null area 802 (shown in a form of a disc), where the magnets 806 can be disposed at both ends of the array and can be approximately half the size of the magnets 804. These magnets, as shown in FIGS. 8a-c, can be oriented radially (i.e., perpendicular to Z) and in an alternating fashion. The magnets 804, 806 can be permanent magnets having a relatively strong near magnetic field (e.g., causing approximately 6706 ppm perturbation on the area 802) and a relatively weak far magnetic field (e.g., causing approximately 1.76 ppm perturbation on the area 808 (shown as a sphere in FIGS. 8b-c)). The magnets 804, 806 can be arranged in an anti-parallel fashion, e.g., some magnets can be arranged to have their magnetic field aligned with the direction of the main magnetic field and others can be arranged so that their magnetic field is opposite the direction of the main magnet field. Further, as shown in FIG. 8a, the magnets 804, 806 can be oriented radially or perpendicular to the z-direction.

In some implementations, magnets 806(a,b) can be configured to cancel out far field effects on each end of the array of magnets. These smaller magnets can be placed at the edge of the magnet array such that the edge effects of the magnet array are partly or substantially cancelled in the imaging area. "Far-field" or "edge" effects can include magnetic fields that are generally not cancelled by paired magnets as described herein. For example, as described herein, two adjacent anti-parallel magnets can have a general field-cancellation effect between them. But on the outside of the pair (e.g., at an "edge") there may not be cancellation. This "edge effect" can be partially mitigated by providing the smaller magnet, to provide some degree of cancellation, and to thus decrease the severity of the edge effect. The smaller magnet can be physically smaller, have a reduced field strength (e.g., ½, ¼, ¹⁄₁₀, etc.) as compared to the other magnets in the apparatus, or a combination of the two.

Figure 9A:
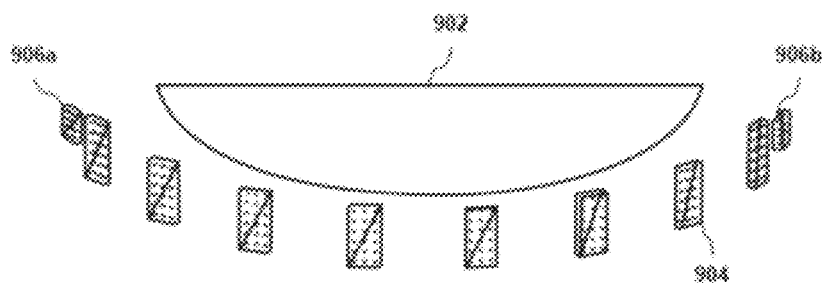
FIGS. 9a-c illustrate another exemplary array of magnets, according to some implementations of the current subject matter.
Figure 9B:
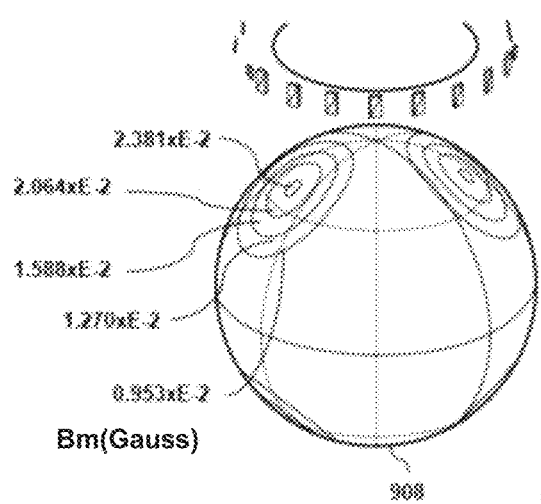
Figure 9C:
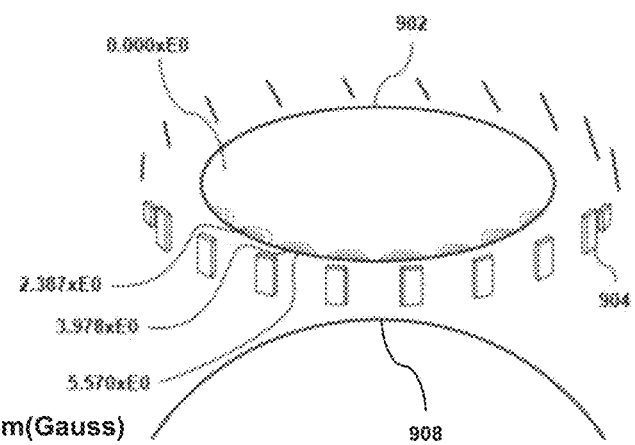

FIGS. 9a-c illustrate another exemplary array of magnets 904 and 906(a, b) that are oriented along a Z direction and arranged around a gradient null area 902 (shown in a form of a disc), where the magnets 906 can be disposed at both ends of the array and can be approximately half the size of the magnets 904. In this case, as shown in FIG. 9a, the magnets 904, 906 can be oriented parallel or along the z-direction (which can, in some cases, be the direction of the MRI magnetic field). Similar to magnets shown in FIGS. 8a-c, the magnets 904, 906 can be permanent magnets having a relatively strong near magnetic field (e.g., causing approximately 1714 ppm perturbation on the area 902) and a relatively weak far magnetic field (e.g., causing approximately 6.86 ppm perturbation on the area 908 (shown as a sphere in FIGS. 9b-c)). The magnets 904, 906 can be arranged in an anti-parallel fashion, e.g., some magnets can be arranged to have their magnetic field aligned with the direction of the main magnetic field and others can be arranged so that their magnetic field is opposite the direction of the main magnet field. In some implementations, the magnets 906 can be configured to cancel out far field effects on each end of the array of magnets.

Figure 11A:
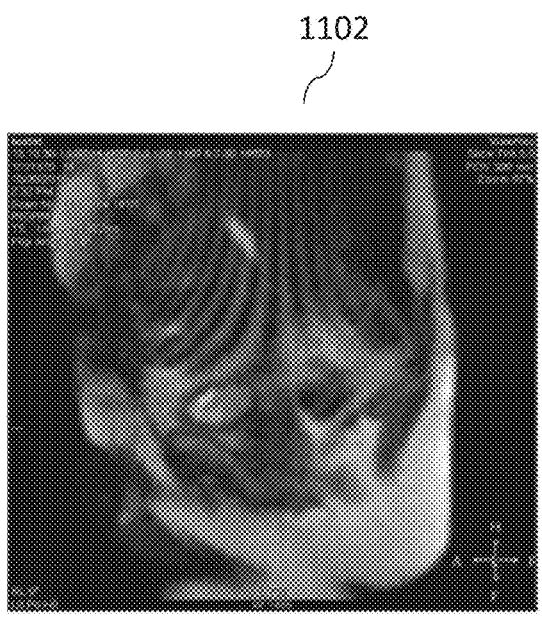
FIG. 11a illustrates an image that was generated by a conventional MRI system.
Figure 11B:
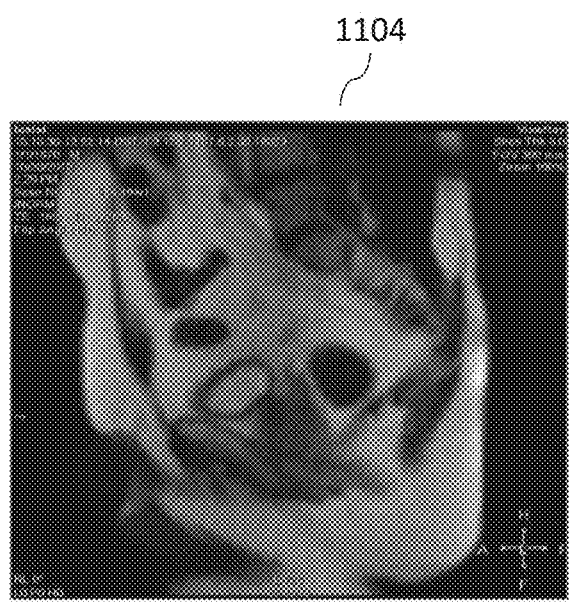
FIG. 11b illustrates an exemplary image of the same object as in FIG. 11a, which was generated using the current subject matter's system for attenuating/removing artifacts.

FIG. 11a illustrates an image 1102 that was generated by a conventional MRI system. The image 1102 includes artefacts (e.g., lines, white spots, etc.). FIG. 11b illustrates an exemplary image 1104 of the same object as in FIG. 11a (i.e., image 1102), which was generated using the current subject matter's system for attenuating/removing artifacts. As shown in FIG. 11b, the artifacts that were present in the image 1102 are absent from image 1104.

Figure 12:
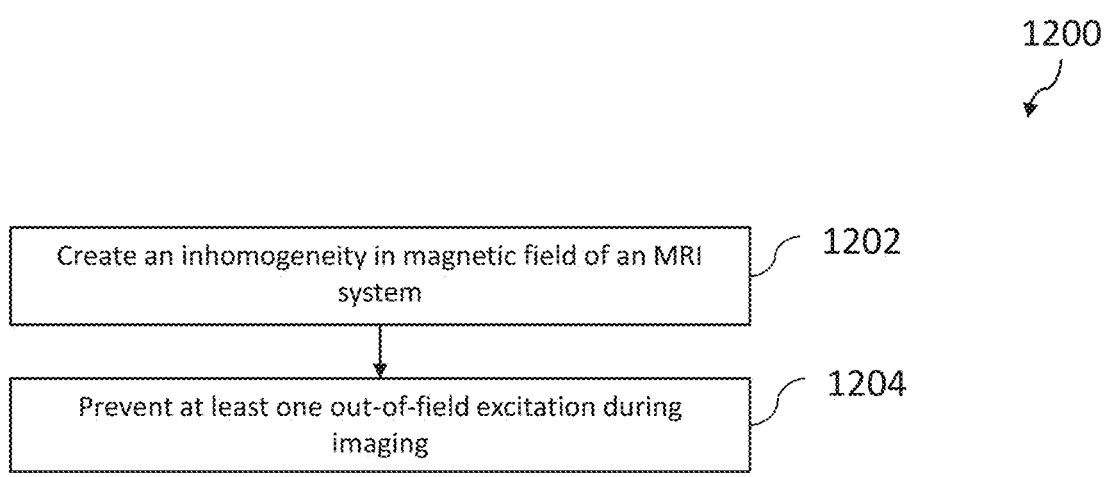
FIG. 12 is a flow chart illustrating an exemplary method, according to some implementations of the current subject matter.

FIG. 12 illustrates an exemplary method 1200 for reducing an appearance of an artifact (which can be caused by a signal produced in the X and Y gradients' null area, as discussed above) in an image generated by a magnetic resonance imaging (MRI) system. The MRI system can include an imaging area and can generate a magnetic field characterized by a main magnetic field gradient. The method 1200 can be performed by a magnetic field generating device, which can include one or more magnets (e.g., a pair of magnets, an array of magnets, etc.), as discussed above. At 1202, the magnetic field generating device can create an inhomogeneity in the MRI magnetic field. At 1204, the device can prevent at least one out-of-field excitation during imaging process performed by the MRI system.

In some implementations, the magnetic field generating device can include at least one permanent magnet, at least one electromagnet, etc., and/or any combination thereof. In some implementations, the magnetic field generating device can include at least one array of magnets. The array of magnets can be arranged on a belt. Further, the magnetic field generating device can be configured to be placed within a patient couch of an MRI system. Alternatively, the magnetic field generating device can be mounted in a bore of the MRI system. Moreover, the magnetic field generating device and a gradient coil of the MRI system can be configured to generate a larger field of view where out-of-field excitation can occur.

In an exemplary implementation where the magnetic field generating device includes an array of magnets (e.g., 2 or more magnets), the array can be positioned in the MRI system outside of the imaging area and corresponding to a location, where X and Y magnetic field gradient(s) are approximately zero. The array's net near magnetic field can be greater than its net far magnetic field by orders of magnitude. Magnets in the array of magnets can be positioned at a first distance away from an isocenter of the magnetic field generated by the MRI system. A first magnet in the array can generate a magnetic field having a direction along a direction of the main magnetic field gradient and a second magnet can generate a magnetic field having a direction opposite the direction of the main magnetic field gradient. The array of magnets can reduce an appearance of the artifact in the image produced by the MRI system.

In some implementations, at least one magnet in the array can be positioned in anti-parallel fashion to at least another magnet in the array of magnets. The magnetic field gradient can include X and/or Y magnetic field gradients. The array can be an array of alternating magnets. At least one magnet in the array can be oriented perpendicular to the magnetic field of the MRI system.

In some exemplary, non-limiting implementations, the first magnet and the second magnet can be positioned a second distance apart. The second distance can be in a range of approximately 1 centimeter to approximately 7 centimeters. The first distance can be in a range of approximately 20 centimeters to approximately 40 centimeters. The first and second magnets in the array can be at least one of the following: identical magnets and different magnets. The net near magnetic field of the array can extend approximately 3 centimeters to approximately 15 centimeters away from the array.

In some implementations, the strength of the magnetic field generated by the first magnet can be substantially equal to the strength of the magnetic field generated by the second magnet. This can produce a cancellation of the magnetic fields generated by the first magnet and the second magnet when the first magnet and the second magnet are positioned at the first distance.

In some implementations, the first magnet and the second magnet can include at least one of the following: a permanent magnet, an electromagnet, a temporary magnet, a metal, an alloy, and any combination thereof. The first magnet and the second magnet can be positioned proximate to a gradient null, which may be outside the imaging area or inside the imaging area.

As used herein, "proximate," such as proximate to a gradient null, means that such a proximate position is aligned with or corresponding to the location of a gradient null, but need not be precisely at that location.

In some implementations, the array of magnets can include a plurality of pairs of magnets, wherein magnets in each pair of magnets in the plurality of pairs of magnets are positioned apart from each other. The array of magnets can be attached to a surface coil of the MRI system. In some implementations, the array of magnets can be coupled to a pad, the pad being coupled to a surface coil of the MRI system. In some exemplary implementations, the array of magnets can be configured to be coupled to a belt. The belt can be configured to be attached to a subject (e.g., a patient) proximate the location of the approximately null magnetic field gradient.

Figure 13A:
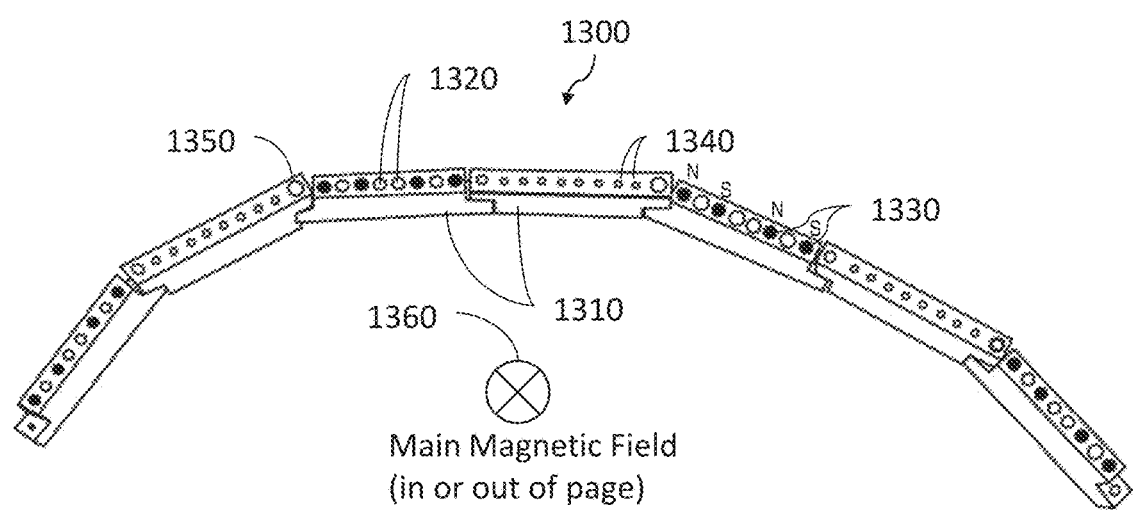
FIG. 13a illustrates an exemplary housing containing an array of magnets, according to some implementations of the present disclosure.

FIG. 13a illustrates an exemplary housing 1300 containing an array of magnets 1330, according to some implementations of the present disclosure. The array of magnets 1330, as described herein for reducing image artifacts, may be implemented as an apparatus positioned within an MRI during imaging. Such implementations can be placed at locations proximate to a gradient null area of the MRI system. Similar to other implementations described herein, the exemplary apparatus of FIG. 13 can include a housing 1300 and array of magnets 1330 contained in the housing. Array of magnets 1330 can have at least a first magnet and a second magnet arranged substantially anti-parallel to the first magnet. Also shown in FIG. 13a is an exemplary orientation of main magnetic field 1360. Main magnetic field 1360 illustrates that array of magnets 1330 (shown with north (N) and south (S) poles) can be oriented substantially along main magnetic field 1360. The polarities shown in FIG. 13a are non-limiting examples. Main magnetic field 1360 can be in other directions and the polarity of magnets 1330 can be in any direction consistent with the instant disclosure.

Housing 1300 can be configured to be at least partially flexible and to provide spacing between the magnets contained therein. In the implementation of FIG. 13, housing 1300 can also include receptacles 1320 for the magnets. The receptacles may be configured to facilitate removal, replacement and reorientation of the magnets contained therein, or can alternatively be configured to permanently receive the magnets.

In the exemplary implementation of FIG. 13, the recesses 1320 are cylindrically shaped, though any other shape can be used to receive an appropriately shaped magnet. Certain implementations may contain holes 1340 extending through an outer surface of housing 1300 to allow air to escape when adding or removing magnets from the recesses (i.e., avoiding pressurized air pockets or vacuums), and to facilitate the removal of magnets by pushing them out with an instrument inserted into holes 1340.

To enable the apparatus to have increased flexibility and/or conform to a patient, the apparatus can be designed with sections 1310. As seen in FIG. 13, sections 1310 can be rigid sections that hold the magnets. Sections 1310 may be connected in a manner allowing the apparatus to be semi-flexible. In some implementations, sections 1310 can be flexibly connected by, for example, hinges 1350, flexible fabric, flexible plastic, rubber, etc.

Figure 13B:
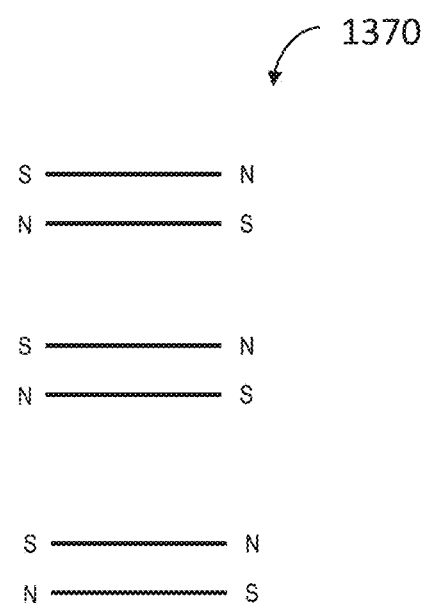
Figure 13C:
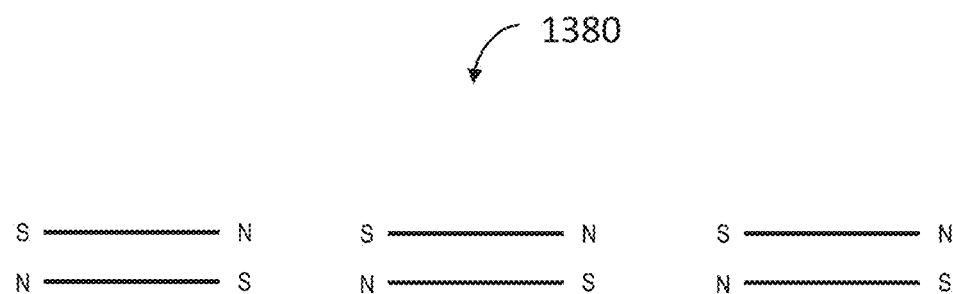
FIG. 13c illustrates an exemplary arrangement of pairs of magnets arranged in an end-to-end configuration, according to some implementations of the present disclosure.

FIG. 13b illustrates an exemplary arrangement of pairs of magnets arranged in a "stacked" configuration 1370, according to some implementations of the present disclosure. FIG. 13c illustrates an exemplary arrangement of pairs of magnets arranged in an "end-to-end" configuration 1380, according to some implementations of the present disclosure. Any number or combination of pairs of magnets can be arranged in a stacked configuration or in an end-to-end configuration. As indicated by the poles, shown in FIGS. 13b, and 13c, a stacked configuration 1370 means a configuration where the directions of the poles of the pairs of magnets are substantially not aligned with the adjacent magnet pairs in the stack. In contrast, an end-to-end configuration 1380 means that the ends of the magnet pairs are arranged such that the poles of the pairs of magnets are more aligned with adjacent magnet pairs. FIG. 13a illustrates an example of an array of magnets 1330 in a stacked configuration.

Figure 14:
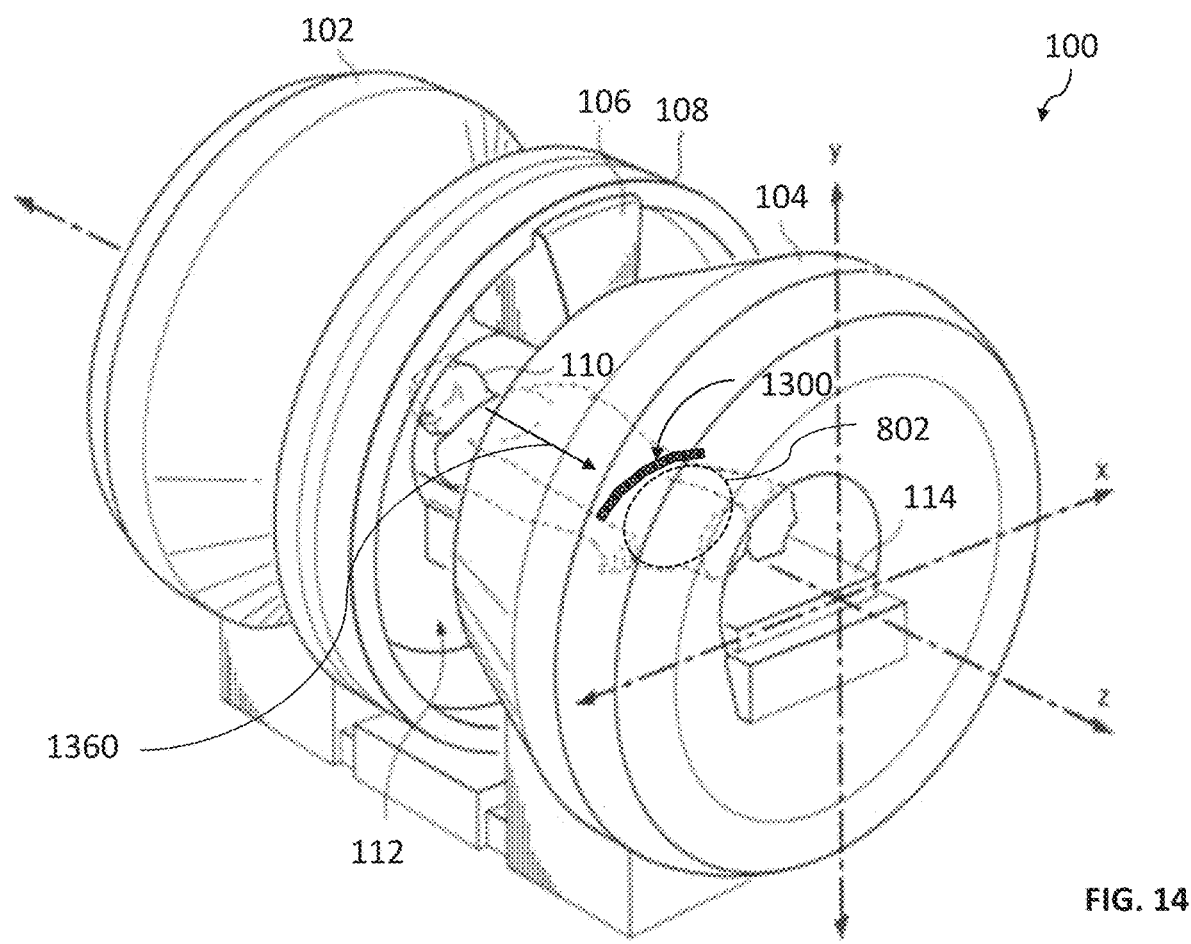
FIG. 14 illustrates the exemplary housing of FIG. 13a, conforming to the shape of a patient, according to some implementations of the present disclosure.

FIG. 14 illustrates the exemplary apparatus 1300 of FIG. 13a conforming to the shape of a patient according to some implementations of the present disclosure. As described herein, the apparatus can be placed proximate the location of a magnetic null, shown in FIG. 14 as area 802. Though shown in FIG. 14 to be inside the MRI and laying across patient 110, the housing 1300 and its array of magnets 1330 may be placed in other locations proximate the gradient null, as described herein.

The descriptions and figures provided herein disclose implementations by way of example and not by way of limitation. All numbers disclosed herein are approximate values unless stated otherwise, regardless whether the word "about" or "approximately" is used in association therewith. Whenever a numerical range with a lower limit and an upper limit is disclosed, any number falling within the range is specifically and expressly disclosed.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and sub-combinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed:

1. An apparatus for reducing appearance of artifacts in magnetic resonance imaging (MRI), comprising: a magnetic field generating device comprising at least one array of magnets, wherein the at least one array of magnets is provided for: creating an inhomogeneity in a magnetic field of an MRI system at a gradient null area outside of an area of interest; and preventing at least one excitation outside the area of interest of a subject during imaging.

2. The apparatus according to claim 1, the array of magnets including at least one permanent magnet or at least one electromagnet.

3. The apparatus according to claim 2, wherein the array of magnets is arranged on a belt.

4. The apparatus according to claim 2, wherein the MRI system includes an imaging area and generates a magnetic field characterized by a main magnetic field gradient; the array of magnets has a net near magnetic field being greater than a net far magnetic field of the array of magnets; the array of magnets is positioned in the MRI system outside of the imaging area and corresponding to a location of an approximately null magnetic field gradient; each magnet in the array of magnets is positioned at a first distance away from an isocenter of the magnetic field generated by the MRI system; and a first magnet in the array of magnets generates a magnetic field having a direction along a direction of the magnetic field of the MRI system and a second magnet in the array of magnets generates a magnetic field having a direction opposite the direction of the magnetic field of the MRI system.

5. The apparatus according to claim 4, wherein the first magnet and the second magnet are positioned proximate to gradient null outside the imaging area.

6. An apparatus for reducing an appearance of an artifact in an image generated by a magnetic resonance imaging (MRI) system, the MRI system including an imaging area and generates a magnetic field characterized by a main magnetic field gradient, the apparatus comprising: an array of magnets with a net near magnetic field being greater than a net far magnetic field; the array of magnets is positioned in the MRI system outside of the imaging area and corresponding to a location of an approximately null magnetic field gradient; and a first magnet in the array of magnets generates a magnetic field having a direction along a direction of the magnetic field of the MRI system and a second magnet in the array of magnets generates a magnetic field having a direction opposite the direction of the magnetic field of the MRI system; wherein the array of magnets reduces appearance of the artifact in the image produced by the MRI system.

7. The apparatus according to claim 6, wherein the array of magnets is an array of alternating magnets, or wherein at least one magnet in the array of magnets is oriented perpendicular to the magnetic field of the MRI system.

8. The apparatus according to claim 6, wherein the first magnet and the second magnet are positioned proximate to a gradient null outside the imaging area.

9. An apparatus configured to be inside of an MRI system, the apparatus comprising: a housing; and an array of magnets contained in the housing, the array of magnets having at least a first magnet and a second magnet arranged substantially anti-parallel to the first magnet, wherein the array of magnets includes at least four magnet pairs having substantially anti-parallel magnets, the array of magnets configured to prevent at least one excitation in a gradient null area that is outside an area of interest of a subject during imaging with the MRI system.

10. The apparatus of claim 9, wherein the array of magnets create an inhomogeneity in a magnetic field of the MRI system.

11. The apparatus of claim 9, wherein the housing is configured to be at least partially flexible and to provide spacing between the first magnet and the second magnet.

12. The apparatus of claim 11, the housing comprising a plurality of receptacles configured to contain at least the first magnet and the second magnet and are configured to facilitate removal, replacement and reorientation of magnets contained therein.

13. The apparatus of claim 12, wherein the housing includes a plurality of sections connected to cause the apparatus to be semi-flexible.

14. The apparatus of claim 13, wherein the plurality of sections are rigid and connected by one or more hinges.

15. The apparatus of claim 9, wherein the first magnet is comprised of a metal that is substantially unmagnetized in the absence of an external magnetic field.

16. The apparatus of claim 15, wherein the first magnet is oriented such that it will be magnetized substantially anti-parallel to the second magnet by an external main magnetic field of a magnetic resonance imaging system.

17. The apparatus of claim 10, the array of magnets comprising a plurality of pairs of magnets in a stacked configuration.

18. The apparatus of claim 17, wherein the plurality of pairs of magnets in the stacked configuration comprises at least three pairs of magnets.

19. The apparatus of claim 9, wherein the array of magnets includes a third magnet and a fourth magnet partially canceling an edge effect of the array of magnets.

20. The apparatus of claim 19, wherein the third magnet and the fourth magnet are smaller than at least one of the first magnet and second magnet.

21. The apparatus of claim 9, the apparatus included in a system further comprising: the MRI system including an imaging area configured to generate a magnetic field characterized by a main magnetic field gradient; wherein the apparatus is positioned at a location within the MRI system that corresponds to where the main magnetic field gradient is approximately null; wherein the apparatus is configured to reduce image artifacts in the MRI system.

22. The apparatus of claim 21, wherein the apparatus is mounted in a bore of the MRI system.

23. The apparatus of claim 21, wherein the apparatus is positioned on a surface coil of the MRI system.

24. The apparatus of claim 21, wherein the apparatus is positioned in a patient couch of the MRI system.

25. The apparatus of claim 10, wherein the array of magnets includes a plurality of magnet pairs having substantially anti-parallel magnets.

* * * * *